United States Patent
Balducci et al.

(10) Patent No.: US 10,150,979 B2
(45) Date of Patent: Dec. 11, 2018

(54) PURIFICATION OF SECRETED POLYSACCHARIDES FROM S. AGALACTIAE

(71) Applicant: GLAXOSMITHKLINE BIOLOGICALS SA, Rixensart (BE)

(72) Inventors: Evita Balducci, Siena (IT); Francesco Berti, Siena (IT); Valdemar Robert Janulczyk, Siena (IT); Immaculada Margarit Y Ros, Siena (IT); Chiara Toniolo, Siena (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 40 days.

(21) Appl. No.: 15/309,283

(22) PCT Filed: May 5, 2015

(86) PCT No.: PCT/EP2015/059773
§ 371 (c)(1),
(2) Date: Nov. 7, 2016

(87) PCT Pub. No.: WO2015/169774
PCT Pub. Date: Nov. 12, 2015

(65) Prior Publication Data
US 2017/0073716 A1    Mar. 16, 2017

(30) Foreign Application Priority Data
May 7, 2014   (EP) .................................. 14167448

(51) Int. Cl.
*C12P 19/04*   (2006.01)
*A61K 39/09*   (2006.01)
*C07K 14/315*  (2006.01)
*C08B 37/00*   (2006.01)

(52) U.S. Cl.
CPC ............ *C12P 19/04* (2013.01); *A61K 39/092* (2013.01); *C07K 14/315* (2013.01); *C08B 37/006* (2013.01)

(58) Field of Classification Search
None
See application file for complete search history.

(56) References Cited

FOREIGN PATENT DOCUMENTS

| WO | 01/68903 A1 | 9/2001 |
| WO | 2006/065137 A2 | 6/2006 |

OTHER PUBLICATIONS

Hanson, et al., Functional Analysis of the CpsA Protein of *Streptococcus agalactiae*, J Bacteriol (2012) 194 (7):1668-1678.
International Search Report for Application No. PCT/EP2015/059773 filed May 5, 2015.
Written Opinion for Application No. PCT/EP2015/059773 filed May 5, 2015.
Cieslewicz et al., (2001) "Functional analysis in type Ia group B *Streptococcus* of a cluster of genes involved in extracellular polysaccharide production by diverse species of streptococci." J. Biol. Chem.; 2001; pp. 139-146; vol. 276.
Deng, et al. "Characterization of the linkage between the type III capsular polysaccharide and the bacterial cell wall of group B *Streptococcus*." J. Biol. Chem.; 2000; pp. 7497-4504; vol. 275(11).
Eberhardt, et al., "Attachment of capsular polysaccharide to the cell wall in *Streptococcus pneumoniae*." Microb. Drug Resist. 2012; pp. 240-255; vol. 18(3).
Hanson, et al., "Membrane topology and DNA binding ability of the streptococcal CpsA protein" J. Bacteriol.; 2011; pp. 411-420; vol. 193(2).
Morona, et al., "Tyrosine phosphorylation of CpsD negatively regulates capsular polysaccharide biosynthesis in *Streptococcus pneumoniae*." Mol. Microbiol.; 2000; pp. 1431-1442; vol. 35(6).
Rubens, et al., "Identification of cpsD, a gene essential for type III capsule expression in group B streptococci." Mol. Microbiol.; 1993; pp. 843-855; vol. 8(5).

*Primary Examiner* — Suzanne M Noakes
(74) *Attorney, Agent, or Firm* — Virginia G. Campen

(57) ABSTRACT

The invention relates to bacterial mutants, particularly from *Streptococcus agalactiae*, that secrete capsular polysaccharide and methods of purifying the secreted bacterial capsular polysaccharides from culture medium. The extracted polysaccharides are useful for producing vaccines comprising the polysaccharides alone or conjugated to proteins.

42 Claims, 5 Drawing Sheets
Specification includes a Sequence Listing.

PURIFICATION OF SECRETED POLYSACCHARIDES FROM S. AGALACTIAE

This application is filed pursuant to 35 U.S.C. § 371 as a United States National Phase Application of International Patent Application Serial No. PCT/EP2015/059773 filed 5 May 2015, which claims priority to European Application No. EP 14167448.1 filed 7 May 2014, and the entire contents of each of the foregoing applications are hereby incorporated by reference.

FIELD OF THE INVENTION

This invention relates to bacterial mutants, particularly from *Streptococcus agalactiae*, which secrete capsular polysaccharide and methods of purifying the secreted bacterial capsular polysaccharides from culture medium. The extracted polysaccharides are useful for producing vaccines comprising the polysaccharides alone or conjugated to proteins.

BACKGROUND OF THE INVENTION

In the last 25 years, conjugate vaccines, comprising bacterial capsular polysaccharides (CPS) conjugated to protein carriers have been developed. Capsular polysaccharides are important immunogens found on the surface of bacteria involved in various bacterial diseases. This feature has led to them being an important component in the design of vaccines. As saccharides are T-independent antigens, generally CPS are poorly immunogenic. Conjugation to a carrier can convert T-independent antigens into T-dependent antigens, thereby enhancing memory responses and allowing protective immunity to develop.

Therefore, the most effective saccharide vaccines are based on glycoconjugates. Examples include, amongst others, the *Haemophilus influenzae* type b (Hib) conjugate vaccine, conjugate vaccines against *Streptococcus pneumoniae* and serogroup C *Neisseria meningitidis* (MenC). Another bacterium for which conjugate vaccines have been described is *Streptococcus agalactiae*, also known as 'Group B streptococcus', or simply 'GBS'. The 'B' in 'GBS' refers to the Lancefield classification which is based on the antigenicity of a carbohydrate which is soluble in dilute acid and called the C carbohydrate. Lancefield identified 13 types of C carbohydrate (designated A to O) that could be serologically differentiated. The organisms that most commonly infect humans are found in groups A, B, D, and G. Within group B, strains of *Streptococcus agalactiae* are divided into 10 serotypes (Ia, Ib, II, III, IV, V, VI, VII, VIII and IX) based on the structure of their polysaccharide capsule.

Group B *Streptococcus agalactiae* causes serious disease, bacteremia and meningitis, in immunocompromised individuals and in neonates. There are two main types of neonatal GBS infection. Early onset disease occurs within 5 days of birth and is manifested by bacteremia (sepsis or infection of the blood) and pneumonia (an infection of the lungs). Late onset disease occurs from the first week of birth up to around three months after birth. Late onset disease is commonly characterized by meningitis (infection of the fluid and lining around the brain) although bacteremia and pneumonia may also occur. GBS colonises the vagina of about 25 percent of young women and is contracted vertically as a baby passes through the birth canal. Approximately 1 percent of infants born via a vaginal birth to colonised mothers will become infected with a mortality rate of between 50-70 percent.

Investigations have been conducted into the development of protein-based and polysaccharide-based vaccines against GBS. Conjugates of each of the capsular polysaccharides vaccines from GBS serotypes Ia, Ib, II, III, and V have been shown to be safe and immunogenic in humans. For example, vaccination of pregnant women with type III CPS has been demonstrated to reduce the incidence of the late onset meningitis—infants acquire protective antibodies via placental transfer and are passively immunised.

Large-scale production of capsular polysaccharide vaccines requires adequate supplies of purified capsular polysaccharides. Methods for isolating capsular polysaccharides from bacterial cells exist in the art. For example: EP0038265 discloses a method of preparing antigenic polysaccharides which comprises phenolizing the fermentation broth to lyse bacteria and release polysaccharide into the fermentation broth. EP0302887 discloses extraction of GBS type III polysaccharide by the general technique of Jennings et al. (Canadian J. Biochem. 58:112-120 (1980)).

EP1664319 describes a method for producing polysaccharide which comprises: a) using a cationic detergent to precipitate the polysaccharide or part of the contaminants from the supernatant to obtain a first polysaccharide fraction; b) using alcohol to precipitate the polysaccharide from the first polysaccharide fraction to obtain a second polysaccharide fraction; c) subjecting the second polysaccharide fraction to an alcohol precipitation in the presence of an anionic detergent, whereby the alcohol is present in a concentration which is below the concentration at which the polysaccharide precipitates; d) precipitating the polysaccharide from the soluble fraction using alcohol to obtain a polysaccharide precipitate; e) dissolving the polysaccharide precipitate and subjecting it to concentration and diafiltration.

EP1828230 describes a process for heterologous expression and secretion of complex polysaccharides in non-pathogenic, non-invasive Gram-positive bacteria.

EP1951887 and EP2004223 relate to novel strains of *Staphylococcus aureus* that produce type 5 capsular polysaccharide at greater levels than wild-type bacteria.

EP1051506 discloses a method for purifying capsular polysaccharides from cellular components of bacteria and culture supernatants. The method utilises alkaline treatment to lyse bacteria but this also causes hydrolysis of the base labile bond that connects the capsular polysaccharide to cellular components it also deacetylates N-acetyl groups.

However, the above methods require many steps of purification, made more complex by attachment of capsular polysaccharide to the cell wall. It is therefore the object of the invention to provide improved methods for producing capsular polysaccharides without the need for bacterial lysis or enzymatic treatment to release polysaccharide thereby simplifying purification and increasing yield.

SUMMARY OF THE INVENTION

The inventors provide a simplified method of production that makes it possible to obtain capsular polysaccharide from the culture medium in significantly greater quantities than was previously possible. By extracting capsular polysaccharide from the culture medium, the method avoids the need for bacterial inactivation and lysis thereby reducing complexity of the method and the length of time required. Advantageously, CpsA and CpsD mutants exhibit reduced virulence such that the risks associated with handling the bacteria are reduced. Similarly, avoiding the use of base extraction results in increases in operator safety whilst maintaining immunogenicity of extracted polysaccharides because the method avoids deacetylation of N-acetyl groups.

Thus, in a first aspect of the invention there is provided a method for producing a capsular polysaccharide from *Streptococcus agalactiae* comprising: culturing a CpsA or CpsD mutant in a suitable culture medium and recovering the polysaccharide from the culture medium. CpsA and CpsD mutants of the present invention exhibit increased secretion of capsular polysaccharide compared to the wild-type strain.

In a second aspect of the invention, there is provide an isolated polysaccharide from *Streptococcus agalactiae* wherein the polysaccharide has a molecular weight, particularly an average molecular weight, of greater than 800 kDa, greater than 900 kDa, greater than 1000 kDa, greater than 1100 kDa, greater than 1200 kDa, greater than 1300 kDa, greater than 1400 kDa, greater than 1500 kDa, greater than 1600 kDa, about 1700 kDa, particularly about 1758 kDa or any range there between.

DETAILED DESCRIPTION OF THE INVENTION

Figure 1:
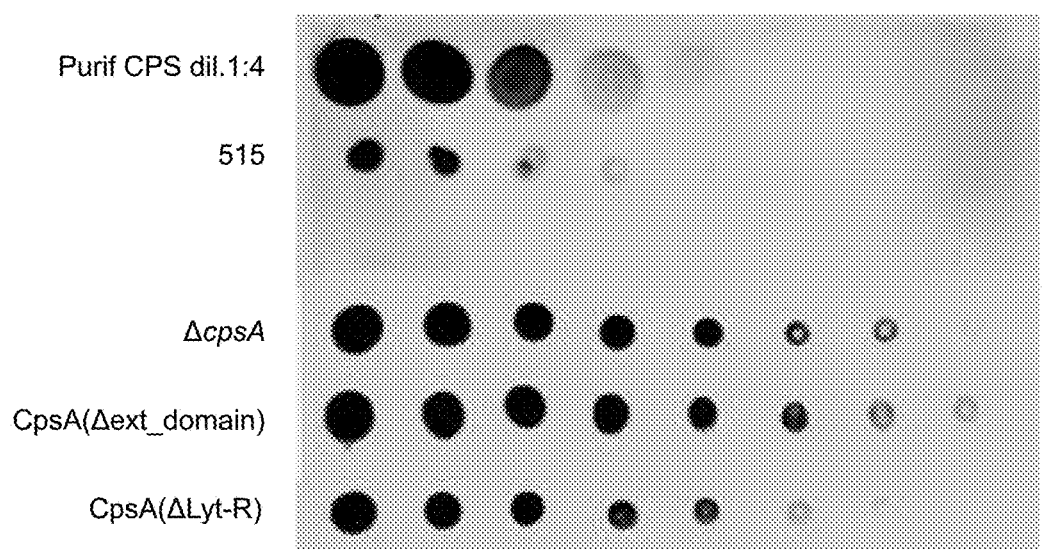
FIG. 1: Dot blot with anti Ia capsular polysaccharide monoclonal antibody of secreted capsular polysaccharide. CpsA mutants secreted significantly greater quantities of polysaccharide in comparison with wild-type bacteria (strain 515).
Figure 2:
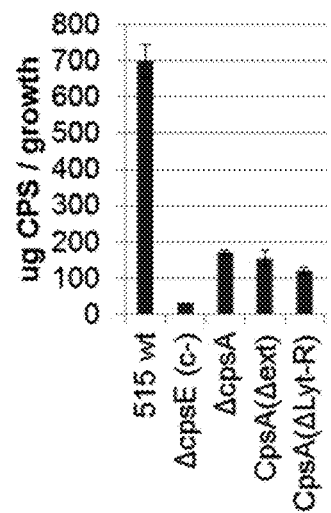
FIG. 2: CpsA mutants have significantly less capsular polysaccharide attached to the bacterial cell surface in comparison to wild-type bacteria (strain 515).
Figure 3:
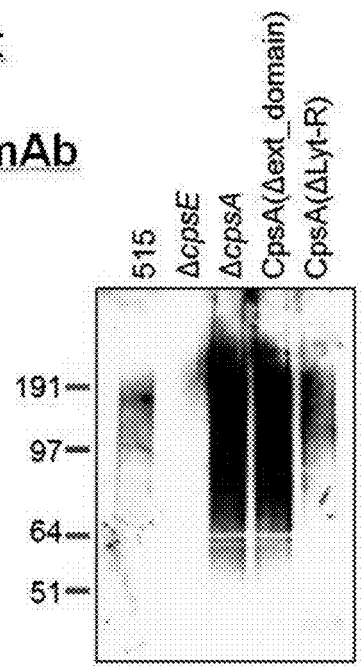
FIG. 3: CpsA mutants secrete significantly greater amounts of capsular polysaccharide having a broader range of sizes (kDa).
Figure 4:
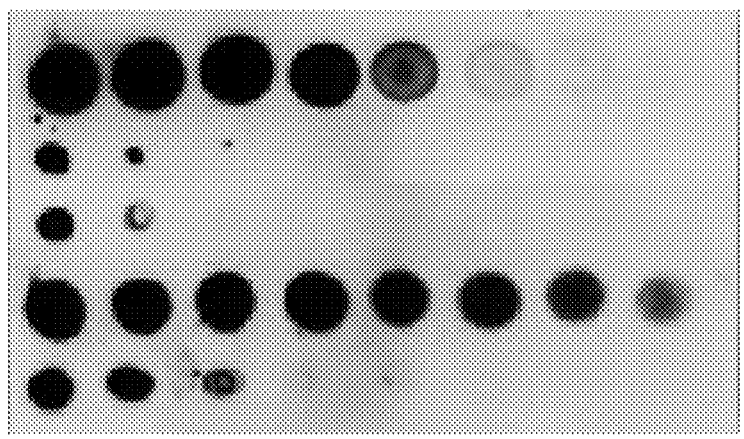
FIG. 4: Dot blot with anti Ia capsular polysaccharide monoclonal antibody of secreted capsular polysaccharide. CpsD mutants secreted greater quantities of polysaccharide in comparison with wild-type bacteria (strain 515). Of the exemplified mutants, the K49 and ΔP-tyr secreted greater quantities than both wild-type and ΔCpsD. Thus, preferred mutations occur in the autokinase active site.
Figure 5:
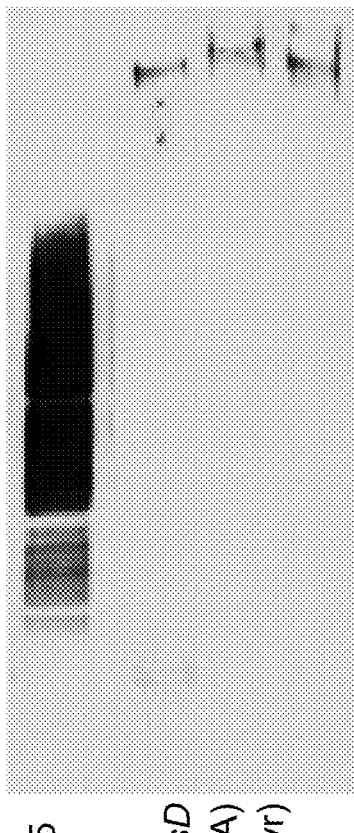
FIG. 5: CpsD mutants secrete significantly greater amounts of capsular polysaccharide having a greater size than that secreted by wild-type strain 515 (kDa).

By introducing mutations into the sequence of the CpsA or CpsD polynucleotide and/or protein, the present inventors have surprisingly discovered that such bacteria produce greater quantities of capsular polysaccharide and that the capsular polysaccharide is secreted into the culture medium.

The recombinant *Streptococcus agalactiae* strains secrete an amount of capsular polysaccharide, in mg/l, as determined by the methods described in the Examples, that is greater than that secreted by the wild-type strain cultured under the same culturing conditions. Particularly such mutants exhibit an increase in the level or amount of capsular polysaccharide secreted into the culture medium. Particularly the amount or level is at least 10 percent, at least 20 percent, at least 30 percent, at least 40 percent, at least 50 percent, at least 60 percent, at least 70 percent at least 80 percent, at least 90 percent, at least 100 percent or greater than a wild-type cell of the same serotype. Yet more particularly such mutants exhibit a decreased amount of capsular polysaccharide attached to the cell wall. Particularly an amount or level of less than 10 percent, less than 20 percent, less than 30 percent, less than 40 percent, less than 50 percent, less than 60 percent, less than 70 percent or less than 80 percent that of a wild-type cell of the same serotype.

In the context of the present invention, the term "capsular polysaccharide" is intended to mean the capsular polysaccharides of *Streptococcus agalactiae*. In GBS, one of the most important virulence factors is the capsular polysaccharide. To date, ten capsular capsule polysaccharide serotypes have been found: Ia, Ib, II, III, IV, V, VI, VII, VIII and IX.

Capsular Saccharides

The capsular saccharide of *Streptococcus agalactiae* is covalently linked to the peptidoglycan backbone of GBS, and is distinct from the group B antigen, which is another saccharide that is attached to the peptidoglycan backbone. The GBS capsular saccharides are chemically related, but are very different from an antigenic standpoint. All GBS capsular polysaccharides share the following trisaccharide core:

B-D-GlcpNAc(1→3)β-D-Galp(1→4)β-D-Glcp

The various GBS serotypes differ by the way in which this core is modified. The difference between serotypes Ia and III, for instance, arises from the use of either the GlcNAc (Ia) or the Gal (III) in this core for linking consecutive trisaccharide cores. Serotypes Ia and Ib both have a [αD NeupNAc(2→3)βD Galp (1→] disaccharide linked to the GlcNAc in the core, but the linkage is either 1→4 (Ia) or 1→3 (Ib). GBS-related diseases arise primarily from serotypes Ia, Ib, II, III, IV, V, VI, VII, and VIII, with over 85% being caused by five serotypes: Ia, Ib, II, III & V. The invention preferably relates to a saccharide from one or more of these five serotypes, particularly from one or more of serotypes II and V. The capsular saccharides generally include: (a) a terminal N-acetyl-neuraminic acid (NeuNAc) residue (commonly referred to as sialic acid), which in all cases is linked 2→3 to a galactose residue; and (b) a N-acetyl-glucosamine residue (GlcNAc) within the trisaccharide core.

When the GBS saccharide has been purified by base extraction, then O-acetylation is typically lost. Particularly, capsular polysaccharides extracted by the methods of the invention are fully O-acetylated and/or N-acetylated are not de-acetylated (partially or fully). The effect of de-acetylation etc. can be assessed by routine assays.

Particularly the degree of sialic acid oxidation of the GBS capsular polysaccharide is not less than 10%, 20%, 30%, 40%, 50%, 60%, 70%, 80%, 85%, 90%, 95% and particularly the N-acetyl-neuraminic acid (NeuNAc or sialic acid) content of the GBS serotype V capsular polysaccharide is greater than 50%, greater than 60%, greater than 70%, greater than 75%, greater than 80%, greater than 85%, greater than 90%, greater than 95%, when compared to native GBS serotype polysaccharide wherein the NeuNAc content is considered to be about 100%. Particularly, the GBS polysaccharide is a fully sialylated or "native polysaccharide". For example, with a sialic acid content of about 100%, 99%, 98%, 97%, 96%, 95%, 94%, 93%, 92%, 91%, about 90% (or any range between these values) when compared to native GBS polysaccharide.

The saccharide purified according to the invention may be shorter or longer than the GBS polysaccharide found in nature or isolated from a wild-type bacterium. Longer polysaccharides may be depolymerised to give shorter fragments e.g. by hydrolysis in mild acid, by heating, by sizing chromatography, etc.

CpsA

An example of a full-length CpsA amino acid sequence includes Uniprot accession number Q9RPC7 having the following amino acid sequence (SEQ ID NO: 2):

```
MSNHSRRQQK KHSHTPLRVI NLFLLVIFIL LSVVSLFLMY

RHHFLAFRHL NVIYGVVIVL IILASLFLCI KNKARIFTTI

ILVLASIFVA TTLYGFKSTI DLTNNLNKTA SYSEIEMSVI

VPKDSKITNI EAVSKLAAPV KNDTSNITDL IEHIKSEKGI

SITPQKTDSY QDAYNRIKNG DSQAMVLNNA YVSLIELSTP

DFKSQIKTIY TYKIKKKINR KNTNHKEGVF NIYISGIDTF

GSISTVSRSD VNIIMTVNTN THKVLLTTTP RDAYVKIPDG

GGNQYDKLTH AGLYGVETSM KTLENLYDIN LDYYARINFS

SFLKLIDLLG GVTVYNDQAF TSKHGNFDFP VGQVTLNSEQ

ALGFVRERYS LQGGDNDRGR NQEKVIAAII NKLASSQSVT

KLNSITSQLQ TSVQTNMTID NINDLINNQL STGQRFTVES

QALTGHGSTG ELPSYAMPGA QLYMMSIDQS SLSNAKSKIK

NTMEE-
```

In some embodiments, the present invention is based on mutating the CpsA gene by in-frame deletion or other mutation such as substitutions. An in-frame deletion of the CpsA gene can include any truncation of any part of the CpsA gene. In-frame deletions according to the present invention include deletions which remove a segment of the protein coding sequence, yet retain the proper reading frame after the deletion. Some embodiments of the present invention can include deletions that are "clean deletions" i.e., they contain no exogenous DNA sequences inserted into the gene or an in-frame deletion of the CpsA gene may include removal of anywhere from 1 to 485 amino acids. Thus, the inventors have identified residues within SEQ ID NO: 2 that can be modified to alter activity of CpsA such that attachment of capsular polysaccharide to the cell wall is reduced whilst secretion or release of capsular polysaccharide into the external environment, for example, into the culture medium is increased. Moreover, mutation of these residues can be combined with other modifications such as deletions.

CpsA mutants comprise a mutation in the polynucleotide sequence (SEQ ID NO:1) that encodes the CpsA polypeptide sequence set forth in SEQ ID NO: 2, wherein the mutation results in increased secretion of capsular polysaccharide into the culture medium. Particularly the mutation is selected from the group consisting of an in-frame deletion, a point mutation such as a substitution, a deletion, and an insertion.

In certain embodiments, the mutation results in deletion of the polynucleotide sequence that encodes the entire CpsA polypeptide. In other embodiments, the mutation comprises a deletion, wherein the corresponding protein of the deletion mutation lacks at least 2 amino acids. More particularly the mutation comprises a deletion of the part of the polynucleotide sequence that encodes the LytR and/or PFAM region of the CpsA polypeptide. The LytR domain may comprise amino acids 236 to 458 of SEQ ID NO:2, particularly amino acids 248 to 395 of SEQ ID NO:2, particularly the LytR domain may consist of SEQ ID NO:40. The PFAM region or domain of the CpsA polypeptide may comprise or consist of amino acids 72 to 187 of SEQ ID NO:2, particularly the PFAM domain may comprise or consist of SEQ ID NO: 41.

In certain embodiments the CpsA gene comprises a point mutation, particularly a point mutation of one or more of the following residues numbered according to CpsA protein of SEQ ID NO: 2 that causes loss or reduction of CpsA activity and an increase in secretion of capsular polysaccharide: D238, R248, D250, K263, R271, R366, R368, R271, D375, R378, Q382, T437 and E439. Yet more particularly the CpsA gene comprises one or more point mutations from the group consisting of D238, R248, R271 and R366 numbered according to CpsA protein of SEQ ID NO: 2. Not wishing to be bound by theory, the Inventors believe that these residues, which are generally conserved, may be of relevance to substrate binding and/or recognition. Capsular polysaccharides produced by wild-type *Streptococcus agalactiae* have a molecular weight of about 367 kDa. Capsular polysaccharides secreted by CpsA mutants described herein have a molecular weight of greater than 800 kDa. Therefore, invention may also provide purified capsular polysaccharide having a molecular weight, particularly an average molecular weight, of greater than 800 kDa, greater than 900 kDa, greater than 1000 kDa, greater than 1100 kDa, greater than 1200 kDa, greater than 1300 kDa, greater than 1400 kDa, greater than 1500 kDa, greater than 1600 kDa, about 1700 kDa, particularly about 1758 kDa or any range there between.

Analysis of CpsA mutants has revealed that some capsular polysaccharide is attached to the bacterial cell wall, i.e. it is not all secreted. Analysis of such capsular polysaccharide indicates that it has a molecular weight of about 210 kDa. Thus, in certain embodiments capsular polysaccharide may be extracted from the cell wall of CpsA mutants using methods of the prior art to obtain capsular polysaccharide having a molecular weight of less than 300 kDa, less than 250 kDa, particularly about 210 kDa.

CpsD

An example of a full-length CpsD amino acid sequence includes Uniprot accession number K0JNC2 having the following amino acid sequence (SEQ ID NO: 11):

```
MTRLEIVDSK LRQAKKTEEY FNAIRTNIQF SGKENKILAI

TSVREGEGKS TTSTSLALSL AQAGFKTLLI DADTRNSVMS

GTFKATGTIK GLTNYLSGNA DLGDIICETN VPRLMVVPSG

KVPPNPTALL QNAYFNKMIE AIKNIFDYII IDTPPIGLVV

DAAIISNACD GFILVTQAGR IKRNYVEKAK EQMEQSGSKF

LGIILNKVSE SVATYGDYGD YGNYGKRDRK RK
```

In some embodiments, the present invention is based on mutating the CpsD gene by in-frame deletion or other mutation such as substitutions. An in-frame deletion of the CpsD gene can include any truncation of any part of the CpsD gene. In-frame deletions according to the present invention include deletions which remove a segment of the protein coding sequence, yet retain the proper reading frame after the deletion. Some embodiments of the present invention can include deletions that are "clean deletions" i.e., they contain no exogenous DNA sequences inserted into the gene or an in-frame deletion of the CpsD gene may include removal of anywhere from 1 to 232 amino acids. Thus, the inventors have identified residues within SEQ ID NO: 10 that can be modified to alter activity of CpsD such that attachment of capsular polysaccharide to the cell wall is reduced whilst secretion or release of capsular polysaccharide into the external environment, for example, into the culture medium is increased. Moreover, mutation of these residues can be combined with other modifications such as deletions.

CpsD mutants comprise a mutation in the polynucleotide sequence (SEQ ID NO:10) that encodes the CpsD polypeptide sequence set forth in SEQ ID NO: 11, wherein the mutation results in increased secretion of capsular polysaccharide into the culture medium. Particularly the mutation is selected from the group consisting of an in-frame deletion, a point mutation such as a substitution, a deletion, and an insertion.

In certain embodiments, the mutation results in deletion of the polynucleotide sequence that encodes the entire CpsD polypeptide. In other embodiments, the mutation comprises a deletion, wherein the corresponding protein of the deletion mutation lacks at least 2 amino acids. More particularly the mutation comprises a deletion of the part of the polynucleotide sequence that encodes the phosphoacceptor site (P-tyr region) of the CpsD polypeptide. Other mutations include a deletion of the region from the C-terminal Tyr to Phe. In certain embodiments the CpsD gene comprises one or more point mutations selected from the group consisting of K49, S50, D73 and P154, for example, by way of non-limiting example, K49M and/or 550A. Particularly, mutations in the autokinase active site, particularly a point mutation at position K49 numbered according to CpsD protein of SEQ ID NO: 11, that cause loss or reduction of CpsD activity and an increase in secretion of capsular polysaccharide are useful. Capsular polysaccharides produced by wild-type *Streptococcus agalactiae* have a molecular weight of about 367 kDa. Capsular polysaccharides secreted by CpsD mutants described herein have a molecular weight of greater than 800 kDa.

Therefore, invention may also provide purified capsular polysaccharide having a molecular weight, particularly an average molecular weight, of greater than 800 kDa, greater than 900 kDa, greater than 1000 kDa, greater than 2000 kDa, greater than 3000 kDa, greater than 4000 kDa, greater than 5000 kDa, greater than 6000 kDa, greater than 7000 kDa, greater than 8000 kDa, greater than 9000 kDa or any range there between.

Variants

Variants of CpsA and CpsD from other strains of *Streptococcus agalactiae* are known and can be easily identified by, for example, use of BLAST searches of the above sequence. Variants of CpsA include by way of non-limiting example, Uniprot accession numbers: M1Y5W8, S9KSV2, S9JM66 and S8YXF5, also referred to as LytR family transcriptional regulator, regulatory protein CpsX, capsular polysaccharide biosynthesis protein CpsX and the like. Variants of CpsD include by way of non-limiting example, Uniprot accession numbers: V6H970, S9NRN3, S9PP30, S9E9Q3, also referred to as Tyrosine protein kinase and capsular polysaccharide transporter and the like.

Thus, the invention is also applicable to allelic variants of the disclosed CpsA and CpsD proteins from *Streptococcus agalactiae*. In some embodiments, the degree of sequence identity is greater than 80%, 90%, 95%, 96%, 97%, 97.5%, 98%, 98.5%, 99%, 99.5% or more. These polypeptides include homologs, orthologs, allelic variants and functional mutants. Typically, 50% identity or more between two polypeptides is considered to be an indication of functional equivalence.

Purification

Starting material: CpsA and CpsD mutants secrete and release large amounts of capsular polysaccharide into the culture medium during bacterial growth, and so the starting material for purification is generally the supernatant from a centrifuged bacterial culture. By use of CpsA or CpsD mutants, it is not necessary to treat the capsulated bacteria themselves to release capsular saccharide. Advantageously, since the method of the invention does not require the use of base reagents such as NaOH, the saccharide produced by methods of the invention is not partially or fully de-N-acetylated and the methods of the invention do not comprise or require a step of N-reacetylation.

Alcoholic precipitation and cation exchange: The GBS capsular saccharide obtained after culture will generally be impure and may be contaminated with bacterial nucleic acids and proteins. The process of the invention utilises alcoholic precipitation. Since base extraction is not used, materials will not need to be neutralised prior to the precipitation, again decreasing the length of time taken to purify the capsular polysaccharide.

The alcohol used to precipitate contaminating nucleic acids and/or proteins is preferably a lower alcohol, such as methanol, ethanol, propan-1-ol, propan-2-ol, butan-1-ol, butan-2-ol, 2-methyl-propan-1-ol, 2-methyl-propan-2-ol, diols, etc. The selection of an appropriate alcohol can be tested empirically, without undue burden, but alcohols such as ethanol and isopropanol (propan-2-ol) are preferred, rather than alcohols such as phenol.

The alcohol is preferably added to the polysaccharide suspension to give a final alcohol concentration of between 10 percent and 50 percent (e.g. around 30 percent). The most useful concentrations are those which achieve adequate precipitation of contaminants without also precipitating the polysaccharide. The optimum final alcohol concentration may depend on the GBS serotype from which the polysaccharide is obtained, and can be determined by routine experiments without undue burden. Precipitation of polysaccharides as ethanol concentrations>50 percent has been observed.

The alcohol may be added in pure form or may be added in a form diluted with a miscible solvent (e.g. water). Preferred solvent mixtures are ethanol:water mixtures, with a preferred ratio of between around 70:30 and around 95:5 (e.g. 75:25, 80:20, 85:15, 90:10).

The saccharide is also treated with an aqueous metal cation. Monovalent and divalent metal cations are preferred, and divalent cations are particularly preferred, such as Mg++, Mn++, Ca++, etc, as they are more efficient at complex formation. Calcium ions are particularly useful, and so the alcohol mixture preferably includes soluble calcium ions. These may be added to a saccharide/alcohol mixture in the form of calcium salts, either added as a solid or in an aqueous form. The calcium ions are preferably provided by the use of calcium chloride.

The calcium ions are preferably present at a final concentration of between 10 and 500 mM e.g. about 0.1 M. The optimum final Ca++ concentration may depend on the GBS serotype from which the polysaccharide is obtained, and can be determined by routine experiments without undue burden.

The alcohol and the cation play different roles (the alcohol is used to precipitate contaminants, whereas the cation stabilises and complexes the saccharide in soluble form) but produce a combined effect. Although the aim is to prepare a mixture of the saccharide, the alcohol and the cation, these three components need not be mixed together simultaneously. Thus the alcohol and cation can be used sequentially or simultaneously. Sequential treatment is preferred, and a particularly preferred process involves addition of the cation to the saccharide followed by addition of the alcohol to the cation/saccharide mixture, although the alcohol can be used before the cation if desired.

After alcoholic precipitation of contaminating proteins and/or nucleic acids, the GBS capsular polysaccharide is left in solution. The precipitated material can be separated from the polysaccharide by any suitable means, such as by centrifugation. The supernatant can be subjected to microfiltration, and in particular to dead-end filtration (perpendicular filtration) in order to remove particles that may clog filters in later steps (e.g. precipitated particles with a diameter greater than 0.22 micrometers). As an alternative to dead-end filtration, tangential microfiltration can be used.

Diafiltration: The process of the invention may involve a step of diafiltration after the precipitation of proteins and/or nucleic acids. Tangential flow diafiltration may be used. The filtration membrane should thus be one that allows passage of impurities while retaining the capsular polysaccharide. A cut-off in the range 10 kDa-30 kDa is typical. Smaller cut-off sizes can be used but higher cut-off sizes advantageously allow removal of other contaminants without leading to loss of the capsular saccharide. At least 1 cycle of diafiltration may be performed e.g. 2, 3, 4, 5, 6, 7, 8, 9, 10, 11 or more.

In some embodiments, the method further comprises a step of removing contaminating nucleic acids and/or proteins. Particularly contaminating nucleic acids and/or proteins may be removed by the use of precipitation. Yet more particularly, contaminating nucleic acids and/or proteins may be removed from the capsular polysaccharide in aqueous form by the use of alcoholic precipitation. When a step of alcoholic precipitation is included, an alcohol and an aqueous metal cation may be used to precipitate the nucleic acids and/or proteins leaving the polysaccharide in solution. When a step of alcoholic precipitation is included, the method may include a further step of separating the precipitated material from the polysaccharide. Particularly the precipitated material may be separated from the polysaccharide by filtration and yet more particularly the method may comprise a step of diafiltration after the precipitation of nucleic acids and/or proteins. In some embodiments the alcohol is ethanol or isopropanol. In some embodiments the aqueous metal cation is $CaCl_2$. Particularly, methods of the invention will comprise one or more steps of filtration, for example, ultrafiltration and/or gel filtration. In particular embodiments, gel filtration using SEPHACRYL® is performed, for example using SEPHACRYL® S-500 gel.

Further treatment of the capsular polysaccharide: The polysaccharide may be further treated to remove contaminants. This is particularly important in situations where even minor contamination is not acceptable (e.g. for human vaccine production). For example, further precipitation steps may be used. Where an aqueous re-solubilisation was performed then this precipitation will typically use an alcohol, as described in the preceding section; conversely, where an alcoholic re-solubilisation was performed then this precipitation will typically use an aqueous cation solution, as described in the preceding section. The precipitated saccharide can then be separated from any remaining aqueous contaminants e.g. by centrifugation. The precipitated material is stable and can be stored for future use. Further rounds of precipitation and filtration can also be performed.

Depth filtration can also be used e.g. as an alternative to centrifugation. Depth filtration will typically be used after solubilisation in alcohol.

The precipitated material may be subjected to vacuum drying. This treatment will typically be used not to stabilise the saccharide for storage, but to dry the saccharide and remove any residual alcohol. The method produces a purified *Streptococcus agalactiae* capsular polysaccharide. Particularly the capsular polysaccharide is a sialylated capsular polysaccharide, in other words it is neither partially nor fully de-N-acetylated. Yet more particularly, about 90%, 91%, 92%, 93%, 94%, 95%, 96%, 97%, 98%, 99% to about 100% of the repeating units of the purified capsular polysaccharide comprise side chains terminated by N-acetylneuraminic acid (sialic acid; Neu5Ac) $\alpha 2,3$ linked to galactose (Gal).

The purified capsular polysaccharide of the invention can be used as an antigen without further modification e.g. for use in in vitro diagnostic assays, for use in immunisation, etc. For immunisation purposes, however, it is preferred to conjugate the saccharide to a carrier molecule, such as a protein. In general, covalent conjugation of saccharides to carriers enhances the immunogenicity of saccharides as it converts them from T-independent antigens to T-dependent antigens, thus allowing priming for immunological memory. Conjugation is a well known technique. Thus the methods of the invention may include the further step of conjugating the purified saccharide to a carrier molecule. The invention may also provide processes for preparing pharmaceutical compositions, comprising the steps of mixing (a) a polysaccharide of the invention (optionally in the form of a conjugate) with (b) a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier.

The pharmaceutical compositions may be packaged into vials or into syringes. The syringes may be supplied with or without needles. A syringe will include a single dose of the composition, whereas a vial may include a single dose or multiple doses. Aqueous compositions of saccharides of the invention are suitable for reconstituting other vaccines from a lyophilised form. Where a composition of the invention is to be used for such extemporaneous reconstitution, the invention provides a process for reconstituting such a lyophilised vaccine, comprising the step of mixing the lyophilised material with an aqueous composition of the invention. The reconstituted material can be used for injection.

General

The term "comprising" encompasses "including" as well as "consisting" e.g. a composition "comprising" X may consist exclusively of X or may include something additional e.g. X+Y. The term "consisting essentially of" means that the composition, method or structure may include additional ingredients, steps and/or parts, but only if the additional ingredients, steps and/or parts do no materially alter the basic and novel characteristics of the claimed composition, method or structure. The term "consisting of" is generally taken to mean that the invention as claimed is limited to those elements specifically recited in the claim (and may include their equivalents, insofar as the doctrine of equivalents is applicable).

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The word "substantially" does not exclude "completely" e.g. a composition which is "substantially free" from Y may be completely free from Y. For example, "substantially free" from Y can be understood as a composition containing not more than 5% Y, not more than 4% Y, not more than 3% Y, not more than 2% Y, not more than 1% Y, or not more than 0.1% Y. Where necessary, the word "substantially" may be omitted from the definition of the invention.

As used herein, unless otherwise clear from context the term "or" is understood to be inclusive and can be used interchangeably with the term "and/or".

The term "mutant" refers to a gene or gene product that displays modifications in sequence and/or functional properties (i.e., altered characteristics) when compared to the wild-type gene or gene product.

All GenBank Accession numbers provided herein are incorporated by reference in the version available on the date of filing the instant application.

The term "recovering" means the isolation of the capsular polysaccharide in different purities, for example between 5% and 100% purity, preferred purities are in the range of 10% and 99%, 20% and 99%, 30% and 99%, 40% and 99%, 50% and 99%, 60% and 99%, 70% and 99%, 80% and 99%, 90% and 99%. Particular purities are greater than 20%, 30%, 40%, 50%, 60%, 70%, 80%, 90%, 95% or 99%. Recovering may also be referred to as extracting or purifying. The term "purity" takes the general meaning used in the art to refer to the percentage of the in-hand, isolated sample is actually capsular polysaccharide.

This invention is further illustrated by the following examples which should not be construed as limiting.

EXAMPLES

Bacterial Strains and Growth Conditions

GBS 515 (Wessels, et al. 1993) and its isogenic derivatives were grown in Todd-Hewitt broth (THB medium; Difco Laboratories) at 37° C., 5% $CO_2$. Tryptic soy broth (Difco Laboratories), 15 g/L agar (TSA) was used as solid medium. Strains were stored at −80° C. in THB medium+15% glycerol. MAX EFFICIENCY® DH5α™ Competent Cells (Invitrogen) and competent HK100 *E. coli* cells prepared in house were used for transformation, propagation, and preparation of plasmids. *E. coli* was grown at 37° C. with agitation (180 rpm) in Luria-Bertani (LB, Difco laboratories) broth, or on 15 g/L agar plates (LBA). Erythromycin (Erm) was used for selection of GBS (1 µg/ml) or *E. coli* (100 µg/ml) containing the pJRS233-(Perez-Casal et al. 1993) derived plasmids used for mutagenesis. Kanamycin (Kan) was used for selection *E. coli* (50 µg/ml) containing the pET24b-derived plasmids (Novagen) used for initial mutagenesis of inserts, prior to transfer into pJRS233.

Construction of CpsA Plasmids for Mutagenesis and Chromosomal Complementation

To prepare each mutant strain, the shuttle vector pJRS233 (Perez-Casal J, et al. 1993) containing the gene locus with an in-frame deletion or a codon substitution was constructed. Mutant strains developed are described in the Table 1:

| Mutant name | Description | Mutated protein |
|---|---|---|
| ΔcpsA | cpsA deletion | Deletion of aa 11-452 (total = 458) |
| CpsA(Δext_domain) | deletion of the CpsA extracellular domain | Deletion of aa 96-458 (total = 458) |
| CpsA(ΔLyt-R) | Deletion of the CpsA LytR domain | Deletion of aa 236-458 |

Primers used are listed in Table 2 below:

| Name | Sequence | Description |
|---|---|---|
| \multicolumn{3}{c}{amplification of cpsA gene + flanking regions} |||
| NotA5Fsoe | TAAAGCGGCCGCCTCTATCACTGACAACAATGG | Forward, 894 bp upstream cpsA start, NotI RS |
| XhA3Rsoe | TATCCTCGAGGAAGAAGTATATTGTGGCGTA | Reverse, 916 bp downstream cpsA end, XhoI RS |
| \multicolumn{3}{c}{ΔcpsA mutagenesis} |||
| KOA5Rsoe | TTGTTGACGGCGCGAATGATTAGACATTGTAA | Reverse, overlapping KOA3Fsoe |
| KOA3Fsoe | TCGCGCCGTCAACAAAAGAACACAATGGAGGAATAAC | Forward, overlapping KOA5Rsoe |
| \multicolumn{3}{c}{CpsA(Δext_domain) mutagenesis} |||
| M1A5Rsoe | TCCATATAAAGTAGTAGCAACGAAAATAGAAGC | Reverse, overlapping M1A3Fsoe |
| M1A3Fsoe | ACTACTTTATATGGATAACAAGAATGATTGATATTCATTC | Forward, overlapping M1A5Rsoe |
| \multicolumn{3}{c}{CpsA(ΔLyt-R) mutagenesis} |||
| M2A5Rsoe | ACCGCTAATATAGATATTAAATACCCCTTCTTTATG | Reverse, overlapping M2A3Fsoe |
| M2A3Fsoe | TCTATATTAGCGGTTAACAAGAATGATTGATATTCATTCTC | Forward, overlapping M2A5Rsoe |

| Name | Sequence | Description |
|---|---|---|
| | qRT-PCR | |
| SAN_1047F | AGGTTTACTTGTGGCGCTTG | Forward, annealing to gyrA |
| SAN_1047R | TCTGCTTGAGCAATGGTGTC | Reverse, annealing to gyrA |
| SAK_1262F | TCAACTGGACAACGCTTCAC | Forward, annealing to cpsA |
| SAK_1262R | AAGTTGAGCTCCTGGCATTG | Reverse, annealing to cpsA |
| SAK_1258F | TGCTCATATGTGGCATTGTG | Forward, annealing to cpsE |
| SAK_1258R | AGAAAAGATAGCCGGTCCAC | Reverse, annealing to cpsE |

Constructs for genes with codon substitutions were prepared using a splicing by overlap extension PCR (SOEing-PCR) strategy. Briefly, the two parts of the gene up- and downstream of the codon substitution were amplified from 515 gDNA using the PfuUltra II Fusion HS DNA Polymerase (Agilent Technologies). 900-1000 bp upstream and downstream the coding sequence of the gene were added to the inserts. Primers used to amplify the two parts of the genes have 15 bp overlapping tails and introduce the codon substitution in the two PCR products that are then joined together by SOEing-PCR. The resulting fragment was ligated into pJRS233 using BamHI and XhoI restriction sites.

Constructs for genes with in-frame deletions were prepared using the Polymerase Incomplete Primer Extension (PIPE) method. Briefly, the gene plus 900-1000 bp up- and downstream the coding sequence were amplified from 515 gDNA and cloned into pET24b using NotI and XhoI (cpsA inserts) or BamHI and XhoI (cpsD inserts) restriction sites. In frame deletions of the genes were developed by amplifying the plasmid using primers with 15 bp overlapping tails annealing at the two sides of the region to delete. Linear plasmids were transformed into HK100 competent cells able to re-circularize the plasmid. The resulting inserts were then transferred into pJRS233 plasmid by restriction digestion and ligation.

Constructs for chromosomal complementation were prepared transferring into pJRS233 the wild type inserts cloned into pET24b.

Construction of CpsD Plasmids for Mutagenesis and Chromosomal Complementation

To prepare each mutant strain, the shuttle vector pJRS233 (Perez-Casal J, et al. 1993) containing the gene locus with an in-frame deletion or a codon substitution was constructed. Mutant strains developed are described in the Table 3:

| Mutant name | Description | Mutated protein |
|---|---|---|
| ΔcpsD | cpsD deletion | Deletion of aa 11-225 (total = 232) |
| CpsD(K49A) | Point mutation in the autokinase active site | Lysine to alanine in position 49 (total = 232) |
| CpsD(ΔP-Tyr) | Phosphoacceptor site C-terminal deletion | Deletion of aa 213-224 (total = 232) |

Primers used are listed in Table 2 below:

| Name | Sequence | Description |
|---|---|---|
| | amplification of cpsD gene + flanking regions | |
| BaD5Fsoe | TTTAGGATCCCAAAAAGAACGGGTGAAGGAA | Forward, 1018 bp upstream cpsA start, BamHI RS |
| XhD3Rsoe | TCTACTCGAGCTACCATTACGACCTACTCTA | Reverse, 966 bp downstream cpsA end, XhoI RS |
| | ΔcpsD mutagenesis | |
| KOD5Rsoe | GCTATCAACTATTTCTAAACGAGTCATTATATTCTC | Reverse, overlapping KOD3Fsoe |
| KOD3Fsoe | GAAATAGTTGATAGCAAAAGGGATAGAAAAAGGAAGTAA | Forward, overlapping KOD5Rsoe |
| | CpsD(K49A) mutagenesis | |
| M1DmutF | GGAAGGGGAAGGAGCATCCACTACTTCA | Reverse, overlapping M1DmutR |
| M1DmutR | TGAAGTAGTGGATGCTCCTTCCCCTTCC | Forward, overlapping M1DmutF |

| Name | Sequence | Description |
|---|---|---|
| CpsD(ΔP-Tyr) mutagenesis | | |
| M2D5Rsoe | AACAGATTCACTAACTTTATTAAGAATAATACCTAAGAAC | Reverse, overlapping M2D3Fsoe |
| M2D3Fsoe | GTTAGTGAATCTGTTGGAAAAAGGGATAGAAAAAGG | Forward, overlapping M2D5Rsoe |
| qRT-PCR | | |
| SAN_1047F | AGGTTTACTTGTGGCGCTTG | Forward, annealing to gyrA |
| SAN_1047R | TCTGCTTGAGCAATGGTGTC | Reverse, annealing to gyrA |
| SAK_1262F | TCAACTGGACAACGCTTCAC | Forward, annealing to cpsA |
| SAK_1262R | AAGTTGAGCTCCTGGCATTG | Reverse, annealing to cpsA |
| SAK_1258F | TGCTCATATGTGGCATTGTG | Forward, annealing to cpsE |
| SAK_1258R | AGAAAAGATAGCCGGTCCAC | Reverse, annealing to cpsE |

Constructs for genes with codon substitutions were prepared using a splicing by overlap extension PCR (SOEing-PCR) strategy. Briefly, the two parts of the gene up- and downstream of the codon substitution were amplified from 515 gDNA using the PfuUltra II Fusion HS DNA Polymerase (Agilent Technologies). 900-1000 bp upstream and downstream the coding sequence of the gene were added to the inserts. Primers used to amplify the two parts of the genes have 15 bp overlapping tails and introduce the codon substitution in the two PCR products that are then joined together by SOEing-PCR. The resulting fragment was ligated into pJRS233 using BamHI and XhoI restriction sites.

Constructs for genes with in-frame deletions were prepared using the Polymerase Incomplete Primer Extension (PIPE) method. Briefly, the gene plus 900-1000 bp up- and downstream the coding sequence were amplified from 515 gDNA and cloned into pET24b using NotI and XhoI (cpsA inserts) or BamHI and XhoI (cpsD inserts) restriction sites. In frame deletions of the genes were developed by amplifying the plasmid using primers with 15 bp overlapping tails annealing at the two sides of the region to delete. Linear plasmids were transformed into HK100 competent cells able to re-circularize the plasmid. The resulting inserts were then transferred into pJRS233 plasmid by restriction digestion and ligation.

Constructs for chromosomal complementation were prepared transferring into pJRS233 the wild type inserts cloned into pET24b.

Construction of Isogenic Mutants and Chromosomally Complemented Strains

An insertion/duplication and excision mutagenesis strategy was used both to obtain the in-frame deletion/codon substitution in the genes and to replace the mutations to obtain the chromosomally complemented strains. Briefly, pJRS233-derived plasmids purified from E. coli were used to transform electrocompetent 515 cells by electroporation. Transformants were selected by growth on TSA+Erm at 30° C. for 48 hours. Integration was performed by growth of transformants at 37° C. (non-permissive temperature for the suicide shuttle vector) with Erm selection. Excision of the integrated plasmid was performed by serial passages in THB at 30° C., and parallel screening for Erm-sensitive colonies on plate. Mutants were verified by PCR sequencing of the loci.

To obtain the chromosomally complemented strains, pJRS233-derived plasmids containing the wild type version of the genes and the flanking 900-1000 bp up- and downstream were purified from E. coli and complementation of the respective mutant strains was performed as described for mutagenesis.

qRT-PCR Analysis

Bacteria were harvested at two time points: at $OD_{600}$=0.4 (log phase) and $OD_{600}$=1.7 (early stationary phase). To rapidly arrest transcription, 10 ml of bacteria were cooled on ice and added to 10 ml of frozen THB medium in a 50 ml conical tube. GBS cells were then collected by centrifugation for 15 min at 4000 rpm, 4° C., and resuspended in 800 µl of TRIzol (Invitrogen). Bacteria were disrupted mechanically by agitation with Lysing matrix B in 2 ml tubes (DBA Italy) using a homogenizer (Fastprep-24, Millipore) for 60 sec at 6.5 m/s for two cycles, and kept on ice for 2 min between the cycles. Samples were then centrifuged for 5 min at 8000×g, 4° C. and RNA was extracted with DIRECT-ZOL™ RNA MiniPrep kit (Zymo Research) according to the manufacturer's instructions. RNA samples were treated with DNase (Roche) for 2 h at 37° C. and further purified using the RNA MiniPrep kit (Qiagen), including a second DNase treatment on the column for 30 min at room temperature (RT), according to the manufacturer's instructions. cDNA was prepared using the Reverse Transcription System (Promega) by using 500 ng of RNA per reaction. Real time quantitative PCR (qRT-PCR) was performed on 50 ng of cDNA that was amplified using LIGHTCYCLER® 480 DNA SYBR Green I Master, (Roche). Reactions were monitored using a LIGHTCYCLER® 480 instrument and software (Roche). Three technical replicates were monitored for each strain/condition analyzed. To quantify cps operon transcription level primers annealing on cpsA and cpsE were used respectively for cpsA mutants. The transcript amounts in each condition were standardized to an internal control gene (gyrA) and compared with standardized expression in the wild-type strain ($\Delta\Delta C_T$ method).

Quantification of the Capsular Polysaccharide Attached to the Cell Surface

An overnight culture was used to inoculate (1:1000) 50 ml of fresh THB and bacteria were grown at 37° C. for 8 hours. GBS cells were collected by centrifugation for 15 min at 4000 rpm at 4° C., resuspended in 1.1 ml of PBS+0.8 M NaOH and incubated at 37° C. for 36 hours. Samples were neutralized and pelleted by centrifugation for 10 min at 4000 rpm, 4° C. 850 µl of the supernatant were diluted in 7.15 ml of water, and centrifuged for 10 min at 4000 rpm at 4° C. 7.2 µl of the supernatant were loaded on a Vivaspin 10 tube (Sartorius Stedim Biotech) which was centrifuged at 4000 rpm until most of the solution passed through the membrane. After two washes with 1 ml of water, the CPS extract was recovered from the membrane and resuspended in 1.6 ml of water. The amount of CPS present in the extract was estimated by measuring the sialic acid content using the colorimetric resorcinol-hydrochloric acid method (Svennerholm et al, 1957). Briefly, 120 µl of extract were mixed with 380 µl of water and 500 µl of freshly prepared solution R3 (resorcinol 0.2%, copper sulfate 0.3 mM, HCl 30% in $H_2O$). Samples were boiled for 20 min and then cooled to room temperature before being transferred into 1 ml cuvettes to measure their absorbance at 564 nm. The sialic acid content of the samples was then calculated using a concomitantly prepared standard curve using serial dilutions of purified sialic acid. CPS extracts were prepared three times from independent growths to minimize the biological variability.

Quantification of the Capsular Polysaccharide Released in the Growth Medium

An overnight culture was used to inoculate (1:1000) 10 ml of fresh THB and bacteria were grown at 37° C. for 8 hours. GBS cells were pelleted by centrifugation for 15 min at 4000 rpm at 4° C., and the growth medium was collected and filtered using a 0.22 µm Nalgene Syringe Filter (Thermo Scientific). The amount of capsular polysaccharide released in the growth medium was estimated by dot blot. Purified serotype Ia CPS 10 mg/ml was used as standard. Eight serial dilutions were prepared in a 96-well plate by diluting the standard and the growth media in PBS (dilution ratios 1:2 for media, 1:4 for the standard). 2 µl of each serial dilution were spotted onto a nitrocellulose membrane. The membrane was dried for 20 min and blocked by soaking in 5% (w/v) skim milk in PBS-Tween 0.05%. The membrane was then probed with a primary mouse monoclonal anti-serotype Ia CPS-CRM conjugated antibody (30E9/B11) used at 1:2000, washed 3 times in PBS-Tween 0.05%, and incubated in 1:15000 of secondary goat anti-mouse antibody conjugated to horseradish peroxidase. Detection was performed using Thermo Scientific Pierce ECL Western Blotting Substrate according to the manufacturer's instructions.

Western Blot on the Capsular Polysaccharide Released in the Growth Medium

20 µl of medium were mixed with 10 µl of 3× NUPAGE® LDS Sample Buffer+Reducing Agent and boiled for 5 min. Then, 20 µl were loaded on a NuPage 4-12% Bis-Tris Gel 1.0 mm, 12 well (Life Technologies) (running buffer: MOPS 1×) and run at 150V until the band corresponding to 28 kDa of the SEEBLUE® Plus2 Pre-stained Protein Standard (Life Technologies) reached the bottom of the gel. The samples separated on the gel were transferred to a nitrocellulose membrane using the IBLOT® 7-Minute Blotting System (Life Technologies). The membrane was blocked blocked by soaking in 5% (w/v) skim milk in PBS-Tween 0.05%. The membrane was then probed with a primary mouse monoclonal anti-serotype Ia CPS-CRM conjugated antibody (30E9/B11) used at 1:2000, washed 3 times in PBS-Tween 0.05%, and incubated in 1:15000 of secondary goat anti-mouse antibody conjugated to horseradish peroxidase. Detection was performed using Thermo Scientific Pierce ECL Western Blotting Substrate according to the manufacturer's instructions.

Purification of Capsular Saccharide from Culture Media

Supernatant from culture medium was collected by centrifugation following culture of group B *streptococcus* CpsA mutants. A mixture of aqueous ethanol (30%) and CaCl2 (0.1M) was added to the culture medium. A precipitate rapidly formed, which was removed by centrifugation. Sialic acid assays showed that the capsular saccharide remained in the supernatant. The supernatant was subjected to dead-end microfiltration in regenerated cellulose filters (0.22 µm cutoff). The supernatant was than subjected to a tangential flow filtration (TFF) using a 30 kDa cut-off cellulose membrane against Tris 50 mM/NaCl 500 mM pH8.8 and followed by diafiltration against NaPi 10 mM, pH7.2. The precipitate was again removed by centrifugation. A further step of gel filtration using Sephacryl S-500 resin was used. The polysaccharide may be recovered as a pool of fractions, that in some cases, are dried, for example, by vacuum drying.

Those skilled in the art will recognize, or be able to ascertain using no more than routine experimentation, many equivalents to the specific embodiments of the invention described herein. Such equivalents are intended to be encompassed by the following claims.

REFERENCES

Wessels, M. R., Paoletti, L. C., Rodewald, A. K., Michon, F., DiFabio, J.,

Jennings, H. J. & Kasper, D. L. (1993) Infect. Immun. 61, 4760-4766.

Perez-Casal J, Price J A, Maguin E, Scott J R. (1993) Mol Microbiol 8, 809-819.

Svennerholm L., (1957) Biochim Biophys Acta. 24(3), 604-611.

INDEX OF SEQUENCE IDs

SEQ ID NO: 1-CpsA DNA sequence
SEQ ID NO: 2-CpsA amino acid sequence
SEQ ID NO: 3-CpsA LytR amino acid sequence (aa236-458)
SEQ ID NO: 4-CpsA ΔLytR polynucleotide sequence
SEQ ID NO: 5-CpsA ΔLytR amino acid sequence
SEQ ID NO: 6-ΔcpsA Nucleotide sequence:
SEQ ID NO: 7-ΔcpsA Amino acid sequence:
SEQ ID NO: 8-CpsA(Δext_domain) Nucleotide sequence:
SEQ ID NO: 9-CpsA(Δext_domain) Amino acid sequence:
SEQ ID NO: 10-cpsD wild type Nucleotide sequence:
SEQ ID NO: 11-cpsD wild type Amino acid sequence:
SEQ ID NO: 12-ΔcpsD Nucleotide sequence:
SEQ ID NO: 13-ΔcpsD Amino acid sequence:
SEQ ID NO: 14-CpsD(K49A) Nucleotide sequence:
SEQ ID NO: 15-CpsD(K49A) Amino acid sequence:
SEQ ID NO: 16-CpsD(ΔP-Tyr) Nucleotide sequence:
SEQ ID NO: 17-CpsD(ΔP-Tyr) Amino acid sequence:
SEQ ID NO: 18-Primer NotA5Fsoe
SEQ ID NO: 19-Primer XhA3Rsoe
SEQ ID NO: 20-Primer KOA5Rsoe
SEQ ID NO: 21-Primer KOA3Fsoe
SEQ ID NO: 22-Primer M1A5Rsoe
SEQ ID NO: 23-Primer M1A3Fsoe
SEQ ID NO: 24-Primer M2A5Rsoe
SEQ ID NO: 25-Primer M2A3Fsoe
SEQ ID NO: 26-Primer BaD5Fsoe
SEQ ID NO: 27-Primer XhD3Rsoe
SEQ ID NO: 28-Primer KOD5Rsoe
SEQ ID NO: 29-Primer KOD3Fsoe
SEQ ID NO: 30-Primer M1DmutF
SEQ ID NO: 31-Primer M1DmutR
SEQ ID NO: 32-Primer M2D5Rsoe
SEQ ID NO: 33-Primer M2D3Fsoe
SEQ ID NO: 34-Primer SAN_1047F
SEQ ID NO: 35-Primer SAN_1047R
SEQ ID NO: 36-Primer SAK_1262F
SEQ ID NO: 37-Primer SAK_1262R SEQ ID NO: 38-Primer SAK_1258F
SEQ ID NO: 39-Primer SAK_1258R SEQ ID NO: 40-CpsA LytR Domain aa248-395
SEQ ID NO: 41-CpsA PPF/PFAM Domain aa72-187

The invention claimed is:

1. A method for producing a capsular polysaccharide from *Streptococcus agalactiae* comprising:
   (a) culturing in a suitable culture medium a *Streptococcus agalactiae* strain comprising a Capsular Polysaccharide biosynthesis protein A (CpsA) gene with a modified polynucleotide sequence that encodes a CpsA polypeptide with reduced activity, wherein the amount of capsular polysaccharide secreted into the culture medium by said *Streptococcus agalactiae* strain is increased compared to the wild-type *Streptococcus agalactiae* strain, and
   (b) purifying secreted capsular polysaccharide from the culture medium.

2. The method of claim 1 wherein the *Streptococcus agalactiae* strain comprises a CpsA nucleotide sequence selected from:
   (a) a CpsA nucleotide sequence consisting of a truncated CpsA sequence;
   (b) a CpsA nucleotide sequence where the nucleotide sequence encoding the LytR domain of SEQ ID NO:40, the LytR domain of SEQ ID NO:3, or the PFAM domain of SEQ ID NO:41 is deleted;
   (c) a CpsA nucleotide sequence having an alteration resulting in a substitution of at least one amino acid residue in the encoded protein, said substitution selected from the group consisting of: R271, R366, D375, R378 and Q382 numbered according to SEQ ID NO:2; and
   (d) a CpsA nucleotide sequence having an alteration resulting in a substitution of at least one amino acid residue in the encoded protein, said substitution selected from the group consisting of: D238, R248, D250, R271 and R368 numbered according to SEQ ID NO:2.

3. The method of claim 1, wherein the *Streptococcus agalactiae* strain exhibits an increase in the amount of capsular polysaccharide secreted into the culture medium that is at least 10 percent more than wild-type *Streptococcus agalactiae* of the same serotype.

4. The method of claim 1, wherein the capsular polysaccharide is from a *Streptococcus agalactiae* serotype selected from the group consisting of Ia, Ib, II, III, IV, V, VI, VII or VIII.

5. The method of claim 1, wherein the secreted capsular polysaccharide has a molecular weight greater than 800 kDa.

6. The method of claim 1, wherein the secreted capsular polysaccharide is neither partially nor fully de-N-acetylated.

7. The method of claim 1, further comprising the step of removing contaminating nucleic acids or proteins from the secreted capsular polysaccharide by the use of precipitation.

8. The method of claim 7, comprising the steps of: (a) removing contaminating nucleic acids or proteins from the secreted capsular polysaccharide in aqueous form by the use of alcoholic precipitation, wherein an alcohol and an aqueous metal cation are used to precipitate the nucleic acids or proteins leaving the polysaccharide in solution; and (b) separating the precipitated material from the capsular polysaccharide to produce a purified capsular polysaccharide.

9. The method of claim 7, wherein the process further comprises a step of diafiltration after the precipitation of nucleic acids or proteins.

10. The method of claim 8, wherein the alcohol is ethanol or isopropanol.

11. The method of claim 10, wherein the aqueous metal cation is $CaCl_2$.

12. The method of claim 7, further comprising one or more steps of filtration.

13. The method of claim 8, further comprising the step of conjugating purified capsular polysaccharide to a carrier molecule.

14. The method of claim 8, further comprising the step of mixing purified capsular polysaccharide with a pharmaceutically acceptable carrier.

15. A method for producing a capsular polysaccharide from *Streptococcus agalactiae* comprising:
  (a) culturing in a suitable culture medium a *Streptococcus agalactiae* strain comprising a Capsular Polysaccharide biosynthesis protein D (CpsD) gene with a modified polynucleotide sequence that encodes a CpsD polypeptide with reduced activity, wherein the amount of capsular polysaccharide secreted into the culture medium by said *Streptococcus agalactiae* strain is increased compared to the wild-type *Streptococcus agalactiae* strain, and
  (b) purifying capsular polysaccharide from the culture medium.

16. The method of claim 15 wherein the *Streptococcus agalactiae* strain comprises a CpsD nucleotide sequence selected from:
  (a) a CpsD nucleotide sequence having an alteration resulting in a substitution of at least one amino acid residue in the autokinase active site, said substitution selected from the group consisting of K49, S50, D73 and P154 numbered according to SEQ ID NO:11, and
  (b) a CpsD nucleotide sequence wherein the polynucleotide sequence that encodes the phosphoacceptor site (P-tyr region) of the CpsD polypeptide is deleted.

17. The method of claim 15, wherein the *Streptococcus agalactiae* strain exhibits an increase in the amount of capsular polysaccharide secreted into the culture medium that is at least 10 percent more than wild-type *Streptococcus agalactiae* of the same serotype.

18. The method of claim 15, wherein the capsular polysaccharide is from a *Streptococcus agalactiae* serotype selected from the group consisting of Ia, Ib, II, III, IV, V, VI, VII or VIII.

19. The method of claim 15, wherein the secreted capsular polysaccharide has a molecular weight greater than 800 kDa.

20. The method of claim 15, wherein the secreted capsular polysaccharide is neither partially nor fully de-N-acetylated.

21. The method of claim 15, further comprising the step of removing contaminating nucleic acids or proteins from the secreted capsular polysaccharide by the use of precipitation.

22. The method of claim 21, comprising the steps of: (a) removing contaminating nucleic acids or proteins from the secreted capsular polysaccharide in aqueous form by the use of alcoholic precipitation, wherein an alcohol and an aqueous metal cation are used to precipitate the nucleic acids or proteins leaving the polysaccharide in solution; and (b) separating the precipitated material from the capsular polysaccharide to produce a purified capsular polysaccharide.

23. The method of claim 21, wherein the process further comprises a step of diafiltration after the precipitation of nucleic acids or proteins.

24. The method of claim 22, wherein the alcohol is ethanol or isopropanol.

25. The method of claim 22, wherein the aqueous metal cation is $CaCl_2$.

26. The method of claim 21, further comprising one or more steps of filtration.

27. The method of claim 22, further comprising the step of conjugating purified capsular polysaccharide to a carrier molecule.

28. The method of claim 22, further comprising the step of mixing purified capsular polysaccharide with a pharmaceutically acceptable carrier.

29. A method for producing a capsular polysaccharide from *Streptococcus agalactiae* comprising:
  (a) culturing in a suitable culture medium a *Streptococcus agalactiae* strain that encodes a CpsD polypeptide having a K49A substitution numbered according to SEQ ID NO:11; and
  (b) recovering secreted capsular polysaccharide from the culture medium.

30. A method for producing a capsular polysaccharide from *Streptococcus agalactiae* comprising:
  (a) culturing in a suitable culture medium a *Streptococcus agalactiae* strain that does not encode a CpsA polypeptide; and
  (b) recovering secreted capsular polysaccharide from the culture medium.

31. A method for producing a capsular polysaccharide from *Streptococcus agalactiae* comprising:
  (a) culturing in a suitable culture medium a *Streptococcus agalactiae* strain comprising a Capsular Polysaccharide biosynthesis protein A (CpsA) gene, modified such that the polynucleotide sequence encoding the CpsA LytR domain is deleted; and
  (b) recovering secreted capsular polysaccharide from the culture medium.

32. The method of claim 1, wherein the amount of capsular polysaccharide secreted into the culture medium by said *Streptococcus agalactiae* strain is increased compared to the wild-type *Streptococcus agalactiae* strain cultured under the same culturing conditions as used for said *Streptococcus agalactiae* strain comprising a modified CpsA gene.

33. The method of claim 1, wherein said *Streptococcus agalactiae* strain is of serotype Ia.

34. The method of claim 33 wherein the amount of serotype Ia capsular polysaccharide secreted into the culture medium is increased compared to *Streptococcus agalactiae* strain 515 cultured under the same culturing conditions as used for said *Streptococcus agalactiae* strain comprising a modified CpsA gene.

35. The method of claim 1, further comprising the step of conjugating purified capsular polysaccharide to a carrier molecule.

36. The method of claim 1, further comprising the step of mixing purified capsular polysaccharide with a pharmaceutically acceptable carrier.

37. The method of claim 15, wherein the amount of capsular polysaccharide secreted into the culture medium by said *Streptococcus agalactiae* strain is increased compared to the wild-type *Streptococcus agalactiae* strain cultured under the same culturing conditions as used for said *Streptococcus agalactiae* strain comprising a modified CpsD gene.

38. The method of claim 15, wherein said *Streptococcus agalactiae* strain is of serotype Ia.

39. The method of claim 38 wherein the amount of serotype Ia capsular polysaccharide secreted into the culture medium is increased compared to *Streptococcus agalactiae* strain 515 cultured under the same culturing conditions as used for said *Streptococcus agalactiae* strain comprising a modified CpsD gene.

40. The method of claim 15, further comprising the step of conjugating purified capsular polysaccharide to a carrier molecule.

41. The method of claim 15, further comprising the step of mixing purified capsular polysaccharide with a pharmaceutically acceptable carrier.

42. A method for producing a capsular polysaccharide from *Streptococcus agalactiae* comprising:

(a) culturing in a suitable culture medium a *Streptococcus agalactiae* strain that does not encode a CpsD polypeptide; and
(b) recovering secreted capsular polysaccharide from the culture medium.

* * *

SEQUENCE LISTING

<160> NUMBER OF SEQ ID NOS: 41

<210> SEQ ID NO 1
<211> LENGTH: 1455
<212> TYPE: DNA
<213> ORGANISM: Streptococcus agalactiae

<400> SEQUENCE: 1

| | | | | | |
|---|---|---|---|---|---|
| atgtctaatc | attcgcgccg | tcaacaaaag | aaacactcac | atacacctct | acgggtgatt | 60 |
| aatttatttc | ttttggtgat | ttttattttg | ttaagtgtag | tctcattatt | tcttatgtat | 120 |
| cgtcaccatt | ttttggcatt | tagacacctg | aacgtcattt | atggagttgt | aattgtttta | 180 |
| atcattttag | caagtttatt | tctttgtatt | aagaataaag | ctagaatttt | tacaactata | 240 |
| attttagtat | tagcttctat | tttcgttgct | actactttat | atggatttaa | gtcaaccatt | 300 |
| gatttgacaa | ataatctaaa | taaaactgct | tcatactctg | aaattgagat | gagtgtaatt | 360 |
| gtaccaaaag | attctaaaat | aaccaatata | gaagctgtca | gcaaattagc | cgcaccagtt | 420 |
| aaaaacgata | cttcaaatat | tactgatttg | atagaacata | taaaatcaga | aaaaggaatc | 480 |
| tctattacac | cacaaaaaac | agattcttac | caggatgcat | acaatagaat | taaaaatggt | 540 |
| gatagtcagg | ctatggtttt | aaataatgct | tatgttagct | taattgaact | tagcaccccct | 600 |
| gatttttaaat | cgcagataaa | aacgattat | acttacaaaa | ttaagaaaaa | aattaatcgt | 660 |
| aaaaatacta | atcataaaga | aggggtattt | aatatctata | ttagcggtat | tgatactttt | 720 |
| ggctctatat | caacagtatc | aagatctgat | gtaaatatta | ttatgacggt | taataccaat | 780 |
| acccacaaag | tattgttaac | gacaacacca | cgagatgcct | atgtaaaaat | tccagatggt | 840 |
| gggggcaatc | aatatgataa | attaacccat | gcaggtttgt | atggcgttga | gacatcaatg | 900 |
| aaaacacttg | aaaaccttta | cgacatcaac | cttgattatt | atgctagaat | taattttttca | 960 |
| tcatttttaa | aattaataga | cctcttggga | ggagtgacag | tttataacga | tcaagctttt | 1020 |
| acaagtaaac | atggtaattt | tgacttccct | gttggtcaag | taacattgaa | ttctgagcag | 1080 |
| gctttgggct | tgttagaga | acgttattct | ctacaaggag | gcgataacga | tagaggtaga | 1140 |
| aatcaagaaa | aagtgattgc | agctattata | aataagttag | cttctagtca | gtcagtaaca | 1200 |
| aaattaaata | gcattaccctc | acagctccaa | acgtccgttc | aaactaatat | gactattgat | 1260 |
| aatattaatg | atttgattaa | caatcaattg | tcaactggac | aacgcttcac | tgtcgagtca | 1320 |
| caagcattaa | ctggtcatgg | ttcaacgggt | gaactccctt | catatgcaat | gccaggagct | 1380 |
| caactttata | tgatgtcaat | tgatcaatct | agcttatcta | atgcaaaatc | aaaaattaag | 1440 |
| aacacaatgg | aggaa | | | | | 1455 |

<210> SEQ ID NO 2
<211> LENGTH: 485
<212> TYPE: PRT
<213> ORGANISM: Streptococcus agalactiae

<400> SEQUENCE: 2

Met Ser Asn His Ser Arg Arg Gln Gln Lys Lys His Ser His Thr Pro
1               5                   10                  15

Leu Arg Val Ile Asn Leu Phe Leu Leu Val Ile Phe Ile Leu Leu Ser
                20                  25                  30

Val Val Ser Leu Phe Leu Met Tyr Arg His His Phe Leu Ala Phe Arg
            35                  40                  45

```
His Leu Asn Val Ile Tyr Gly Val Val Ile Leu Ile Leu Ala
    50              55              60

Ser Leu Phe Leu Cys Ile Lys Asn Lys Ala Arg Ile Phe Thr Thr Ile
65              70              75              80

Ile Leu Val Leu Ala Ser Ile Phe Val Ala Thr Thr Leu Tyr Gly Phe
                85              90              95

Lys Ser Thr Ile Asp Leu Thr Asn Asn Leu Asn Lys Thr Ala Ser Tyr
                100             105             110

Ser Glu Ile Glu Met Ser Val Ile Val Pro Lys Asp Ser Lys Ile Thr
                115             120             125

Asn Ile Glu Ala Val Ser Lys Leu Ala Ala Pro Val Lys Asn Asp Thr
    130             135             140

Ser Asn Ile Thr Asp Leu Ile Glu His Ile Lys Ser Glu Lys Gly Ile
145             150             155             160

Ser Ile Thr Pro Gln Lys Thr Asp Ser Tyr Gln Asp Ala Tyr Asn Arg
                165             170             175

Ile Lys Asn Gly Asp Ser Gln Ala Met Val Leu Asn Asn Ala Tyr Val
                180             185             190

Ser Leu Ile Glu Leu Ser Thr Pro Asp Phe Lys Ser Gln Ile Lys Thr
                195             200             205

Ile Tyr Thr Tyr Lys Ile Lys Lys Ile Asn Arg Lys Asn Thr Asn
    210             215             220

His Lys Glu Gly Val Phe Asn Ile Tyr Ile Ser Gly Ile Asp Thr Phe
225             230             235             240

Gly Ser Ile Ser Thr Val Ser Arg Ser Asp Val Asn Ile Ile Met Thr
                245             250             255

Val Asn Thr Asn Thr His Lys Val Leu Leu Thr Thr Thr Pro Arg Asp
    260             265             270

Ala Tyr Val Lys Ile Pro Asp Gly Gly Asn Gln Tyr Asp Lys Leu
    275             280             285

Thr His Ala Gly Leu Tyr Gly Val Glu Thr Ser Met Lys Thr Leu Glu
    290             295             300

Asn Leu Tyr Asp Ile Asn Leu Asp Tyr Ala Arg Ile Asn Phe Ser
305             310             315             320

Ser Phe Leu Lys Leu Ile Asp Leu Leu Gly Gly Val Thr Val Tyr Asn
                325             330             335

Asp Gln Ala Phe Thr Ser Lys His Gly Asn Phe Asp Phe Pro Val Gly
                340             345             350

Gln Val Thr Leu Asn Ser Glu Gln Ala Leu Gly Phe Val Arg Glu Arg
                355             360             365

Tyr Ser Leu Gln Gly Gly Asp Asn Asp Arg Gly Arg Asn Gln Glu Lys
    370             375             380

Val Ile Ala Ala Ile Ile Asn Lys Leu Ala Ser Ser Gln Ser Val Thr
385             390             395             400

Lys Leu Asn Ser Ile Thr Ser Gln Leu Gln Thr Ser Val Gln Thr Asn
                405             410             415

Met Thr Ile Asp Asn Ile Asn Asp Leu Ile Asn Asn Gln Leu Ser Thr
                420             425             430

Gly Gln Arg Phe Thr Val Glu Ser Gln Ala Leu Thr Gly His Gly Ser
        435             440             445

Thr Gly Glu Leu Pro Ser Tyr Ala Met Pro Gly Ala Gln Leu Tyr Met
    450             455             460
```

Met Ser Ile Asp Gln Ser Ser Leu Ser Asn Ala Lys Ser Lys Ile Lys
465                 470                 475                 480

Asn Thr Met Glu Glu
                485

<210> SEQ ID NO 3
<211> LENGTH: 222
<212> TYPE: PRT
<213> ORGANISM: Streptococcus agalactiae

<400> SEQUENCE: 3

Ile Asp Thr Phe Gly Ser Ile Ser Thr Val Ser Arg Ser Asp Val Asn
1               5                   10                  15

Ile Ile Met Thr Val Asn Thr Asn Thr His Lys Val Leu Leu Thr Thr
            20                  25                  30

Thr Pro Arg Asp Ala Tyr Val Lys Ile Pro Asp Gly Gly Gly Asn Gln
        35                  40                  45

Tyr Asp Lys Leu Thr His Ala Gly Leu Tyr Gly Val Glu Thr Ser Met
    50                  55                  60

Lys Thr Leu Glu Asn Leu Tyr Asp Ile Asn Leu Asp Tyr Tyr Ala Arg
65                  70                  75                  80

Ile Asn Phe Ser Ser Phe Leu Lys Leu Ile Asp Leu Leu Gly Gly Val
                85                  90                  95

Thr Val Tyr Asn Asp Gln Ala Phe Thr Ser Lys His Gly Asn Phe Asp
            100                 105                 110

Phe Pro Val Gly Gln Val Thr Leu Asn Ser Glu Gln Ala Leu Gly Phe
        115                 120                 125

Val Arg Glu Arg Tyr Ser Leu Gln Gly Gly Asp Asn Asp Arg Gly Arg
    130                 135                 140

Asn Gln Glu Lys Val Ile Ala Ala Ile Ile Asn Lys Leu Ala Ser Ser
145                 150                 155                 160

Gln Ser Val Thr Lys Leu Asn Ser Ile Thr Ser Gln Leu Gln Thr Ser
                165                 170                 175

Val Gln Thr Asn Met Thr Ile Asp Asn Ile Asn Asp Leu Ile Asn Asn
            180                 185                 190

Gln Leu Ser Thr Gly Gln Arg Phe Thr Val Glu Ser Gln Ala Leu Thr
        195                 200                 205

Gly His Gly Ser Thr Gly Glu Leu Pro Ser Tyr Ala Met Pro
    210                 215                 220

<210> SEQ ID NO 4
<211> LENGTH: 711
<212> TYPE: DNA
<213> ORGANISM: Streptococcus agalactiae

<400> SEQUENCE: 4
atgtctaatc attcgcgccg tcaacaaaag aaacactcac atacacctct acgggtgatt      60
aatttatttc ttttggtgat ttttattttg ttaagtgtag tctcattatt tcttatgtat     120
cgtcaccatt ttttggcatt tagacacctg aacgtcattt atggagttgt aattgtttta     180
atcattttag caagtttatt tctttgtatt aagaataaag ctagaatttt tacaactata     240
attttagtat tagcttctat tttcgttgct actactttat atggatttaa gtcaaccatt     300
gatttgacaa ataatctaaa taaaactgct tcatactctg aaattgagat gagtgtaatt     360
gtaccaaaag attctaaaat aaccaatata gaagctgtca gcaaattagc cgcaccagtt     420
aaaaacgata cttcaaatat tactgatttg atagaacata taaaatcaga aaaggaatc     480

```
tctattacac cacaaaaaac agattcttac caggatgcat acaatagaat taaaaatggt    540
gatagtcagg ctatggtttt aaataatgct tatgttagct taattgaact tagcacccct    600
gattttaaat cgcagataaa aacgatttat acttacaaaa ttaagaaaaa aattaatcgt    660
aaaaatacta atcataaaga agggtattt aatatctata ttagcggtta a              711
```

<210> SEQ ID NO 5
<211> LENGTH: 236
<212> TYPE: PRT
<213> ORGANISM: Streptococcus agalactiae

<400> SEQUENCE: 5

```
Met Ser Asn His Ser Arg Arg Gln Gln Lys Lys His Ser His Thr Pro
1               5                   10                  15

Leu Arg Val Ile Asn Leu Phe Leu Leu Val Ile Phe Ile Leu Leu Ser
            20                  25                  30

Val Val Ser Leu Phe Leu Met Tyr Arg His His Phe Leu Ala Phe Arg
        35                  40                  45

His Leu Asn Val Ile Tyr Gly Val Val Ile Val Leu Ile Ile Leu Ala
    50                  55                  60

Ser Leu Phe Leu Cys Ile Lys Asn Lys Ala Arg Ile Phe Thr Thr Ile
65                  70                  75                  80

Ile Leu Val Leu Ala Ser Ile Phe Val Ala Thr Thr Leu Tyr Gly Phe
                85                  90                  95

Lys Ser Thr Ile Asp Leu Thr Asn Asn Leu Asn Lys Thr Ala Ser Tyr
            100                 105                 110

Ser Glu Ile Glu Met Ser Val Ile Val Pro Lys Asp Ser Lys Ile Thr
        115                 120                 125

Asn Ile Glu Ala Val Ser Lys Leu Ala Ala Pro Val Lys Asn Asp Thr
    130                 135                 140

Ser Asn Ile Thr Asp Leu Ile Glu His Ile Lys Ser Glu Lys Gly Ile
145                 150                 155                 160

Ser Ile Thr Pro Gln Lys Thr Asp Ser Tyr Gln Asp Ala Tyr Asn Arg
                165                 170                 175

Ile Lys Asn Gly Asp Ser Gln Ala Met Val Leu Asn Asn Ala Tyr Val
            180                 185                 190

Ser Leu Ile Glu Leu Ser Thr Pro Asp Phe Lys Ser Gln Ile Lys Thr
        195                 200                 205

Ile Tyr Thr Tyr Lys Ile Lys Lys Ile Asn Arg Lys Asn Thr Asn
    210                 215                 220

His Lys Glu Gly Val Phe Asn Ile Tyr Ile Ser Gly
225                 230                 235
```

<210> SEQ ID NO 6
<211> LENGTH: 48
<212> TYPE: DNA
<213> ORGANISM: Streptococcus agalactiae

<400> SEQUENCE: 6

```
atgtctaatc attcgcgccg tcaacaaaag aacacaatgg aggaataa              48
```

<210> SEQ ID NO 7
<211> LENGTH: 15
<212> TYPE: PRT
<213> ORGANISM: Streptococcus agalactiae

<400> SEQUENCE: 7

Met Ser Asn His Ser Arg Arg Gln Gln Lys Asn Thr Met Glu Glu
1               5                   10                  15

<210> SEQ ID NO 8
<211> LENGTH: 288
<212> TYPE: DNA
<213> ORGANISM: Streptococcus agalactiae

<400> SEQUENCE: 8

```
atgtctaatc attcgcgccg tcaacaaaag aaacactcac atacacctct acgggtgatt      60
aatttatttc ttttggtgat ttttattttg ttaagtgtag tctcattatt tcttatgtat     120
cgtcaccatt ttttggcatt tagacacctg aacgtcattt atggagttgt aattgtttta     180
atcattttag caagtttatt tctttgtatt aagaataaag ctagaatttt tacaactata     240
attttagtat tagcttctat tttcgttgct actactttat atggataa                  288
```

<210> SEQ ID NO 9
<211> LENGTH: 95
<212> TYPE: PRT
<213> ORGANISM: Streptococcus agalactiae

<400> SEQUENCE: 9

Met Ser Asn His Ser Arg Arg Gln Gln Lys Lys His Ser His Thr Pro
1               5                   10                  15

Leu Arg Val Ile Asn Leu Phe Leu Leu Val Ile Phe Ile Leu Leu Ser
            20                  25                  30

Val Val Ser Leu Phe Leu Met Tyr Arg His His Phe Leu Ala Phe Arg
        35                  40                  45

His Leu Asn Val Ile Tyr Gly Val Val Ile Val Leu Ile Ile Leu Ala
    50                  55                  60

Ser Leu Phe Leu Cys Ile Lys Asn Lys Ala Arg Ile Phe Thr Thr Ile
65                  70                  75                  80

Ile Leu Val Leu Ala Ser Ile Phe Val Ala Thr Thr Leu Tyr Gly
                85                  90                  95

<210> SEQ ID NO 10
<211> LENGTH: 699
<212> TYPE: DNA
<213> ORGANISM: Streptococcus agalactiae

<400> SEQUENCE: 10

```
atgactcgtt tagaaatagt tgatagcaag ttaagacaag caaaaaaaac agaagaatac      60
ttcaatgcga tccgtacaaa catacagttt agtggaaagg aaaataaaat tcttgcaatt     120
acctctgtta gggaagggga aggaaaatcc actacttcaa caagtttagc tttatcttta     180
gctcaagcag gatttaaaac attattaatt gatgcggata ctaggaactc tgttatgtct     240
ggaacctta aagcaactgg aactattaaa ggcttgacga attatttatc aggtaatgca     300
gatcttggag atattatctg tgaaaccaat gttcctagac tgatggtcgt tccttcaggg     360
aaagtaccac caaatccaac agcattactt cagaacgctt attttaataa gatgattgaa     420
gctattaaaa atatatttga ttatattatc atcgatactc cacctattgg tttagttgtt     480
gatgccgcaa taatctctaa tgcttgcgat ggttttattt tagtaaccca agcaggtaga     540
ataaaacgta attatgttga aaaagcaaaa gaacagatgg aacaaagtgg ttcaaagttc     600
ttaggtatta ttcttaataa agttagtgaa tctgttgcta cttacggcga ttacggcgat     660
tatggaaatt acggaaaaag ggatagaaaa aggaagtaa                            699
```

<210> SEQ ID NO 11
<211> LENGTH: 232
<212> TYPE: PRT
<213> ORGANISM: Streptococcus agalactiae

<400> SEQUENCE: 11

```
Met Thr Arg Leu Glu Ile Val Asp Ser Lys Leu Arg Gln Ala Lys Lys
1               5                   10                  15

Thr Glu Glu Tyr Phe Asn Ala Ile Arg Thr Asn Ile Gln Phe Ser Gly
            20                  25                  30

Lys Glu Asn Lys Ile Leu Ala Ile Thr Ser Val Arg Glu Gly Glu Gly
        35                  40                  45

Lys Ser Thr Thr Ser Thr Ser Leu Ala Leu Ser Leu Ala Gln Ala Gly
    50                  55                  60

Phe Lys Thr Leu Leu Ile Asp Ala Asp Thr Arg Asn Ser Val Met Ser
65                  70                  75                  80

Gly Thr Phe Lys Ala Thr Gly Thr Ile Lys Gly Leu Thr Asn Tyr Leu
                85                  90                  95

Ser Gly Asn Ala Asp Leu Gly Asp Ile Ile Cys Glu Thr Asn Val Pro
            100                 105                 110

Arg Leu Met Val Val Pro Ser Gly Lys Val Pro Pro Asn Pro Thr Ala
        115                 120                 125

Leu Leu Gln Asn Ala Tyr Phe Asn Lys Met Ile Glu Ala Ile Lys Asn
    130                 135                 140

Ile Phe Asp Tyr Ile Ile Ile Asp Thr Pro Pro Ile Gly Leu Val Val
145                 150                 155                 160

Asp Ala Ala Ile Ile Ser Asn Ala Cys Asp Gly Phe Ile Leu Val Thr
                165                 170                 175

Gln Ala Gly Arg Ile Lys Arg Asn Tyr Val Glu Lys Ala Lys Glu Gln
            180                 185                 190

Met Glu Gln Ser Gly Ser Lys Phe Leu Gly Ile Ile Leu Asn Lys Val
        195                 200                 205

Ser Glu Ser Val Ala Thr Tyr Gly Asp Tyr Gly Asp Tyr Gly Asn Tyr
    210                 215                 220

Gly Lys Arg Asp Arg Lys Arg Lys
225                 230
```

<210> SEQ ID NO 12
<211> LENGTH: 51
<212> TYPE: DNA
<213> ORGANISM: Streptococcus agalactiae

<400> SEQUENCE: 12
atgactcgtt tagaaatagt tgatagcaaa aaggatagaa aaggaagta a        51

<210> SEQ ID NO 13
<211> LENGTH: 16
<212> TYPE: PRT
<213> ORGANISM: Streptococcus agalactiae

<400> SEQUENCE: 13

```
Met Thr Arg Leu Glu Ile Val Asp Ser Lys Lys Asp Arg Lys Arg Lys
1               5                   10                  15
```

<210> SEQ ID NO 14
<211> LENGTH: 699
<212> TYPE: DNA

<213> ORGANISM: Artificial Sequence
<220> FEATURE:
<223> OTHER INFORMATION: CpsD sequence comprising K49A mutation

<400> SEQUENCE: 14

```
atgactcgtt tagaaatagt tgatagcaag ttaagacaag caaaaaaaac agaagaatac     60
ttcaatgcga tccgtacaaa catacagttt agtggaaagg aaaataaaat tcttgcaatt    120
acctctgtta gggaagggga aggagcatcc actacttcaa caagtttagc tttatcttta    180
gctcaagcag gatttaaaac attattaatt gatgcggata ctaggaactc tgttatgtct    240
ggaacctta aagcaactgg aactattaaa ggcttgacga attatttatc aggtaatgca    300
gatcttggag atattatctg tgaaaccaat gttcctagac tgatggtcgt tccttcaggg    360
aaagtaccac caaatccaac agcattactt cagaacgctt attttaataa gatgattgaa    420
gctattaaaa atatatttga ttatattatc atcgatactc cacctattgg tttagttgtt    480
gatgccgcaa taatctctaa tgcttgcgat ggttttattt tagtaaccca agcaggtaga    540
ataaaacgta attatgttga aaagcaaaa gaacagatgg aacaaagtgg ttcaaagttc    600
ttaggtatta ttcttaataa agttagtgaa tctgttgcta cttacggcga ttacggcgat    660
tatggaaatt acggaaaaag ggatagaaaa aggaagtaa                            699
```

<210> SEQ ID NO 15
<211> LENGTH: 232
<212> TYPE: PRT
<213> ORGANISM: Artificial Sequence
<220> FEATURE:
<223> OTHER INFORMATION: CpsD amino acid sequence comprising K49A mutation

<400> SEQUENCE: 15

```
Met Thr Arg Leu Glu Ile Val Asp Ser Lys Leu Arg Gln Ala Lys Lys
 1               5                  10                  15

Thr Glu Glu Tyr Phe Asn Ala Ile Arg Thr Asn Ile Gln Phe Ser Gly
            20                  25                  30

Lys Glu Asn Lys Ile Leu Ala Ile Thr Ser Val Arg Glu Gly Glu Gly
        35                  40                  45

Ala Ser Thr Thr Ser Thr Ser Leu Ala Leu Ser Leu Ala Gln Ala Gly
    50                  55                  60

Phe Lys Thr Leu Leu Ile Asp Ala Asp Thr Arg Asn Ser Val Met Ser
65                  70                  75                  80

Gly Thr Phe Lys Ala Thr Gly Thr Ile Lys Gly Leu Thr Asn Tyr Leu
                85                  90                  95

Ser Gly Asn Ala Asp Leu Gly Asp Ile Ile Cys Glu Thr Asn Val Pro
            100                 105                 110

Arg Leu Met Val Val Pro Ser Gly Lys Val Pro Pro Asn Pro Thr Ala
        115                 120                 125

Leu Leu Gln Asn Ala Tyr Phe Asn Lys Met Ile Glu Ala Ile Lys Asn
    130                 135                 140

Ile Phe Asp Tyr Ile Ile Ile Asp Thr Pro Pro Ile Gly Leu Val Val
145                 150                 155                 160

Asp Ala Ala Ile Ile Ser Asn Ala Cys Asp Gly Phe Ile Leu Val Thr
                165                 170                 175

Gln Ala Gly Arg Ile Lys Arg Asn Tyr Val Glu Lys Ala Lys Glu Gln
            180                 185                 190

Met Glu Gln Ser Gly Ser Lys Phe Leu Gly Ile Ile Leu Asn Lys Val
        195                 200                 205
```

Ser Glu Ser Val Ala Thr Tyr Gly Asp Tyr Gly Asp Tyr Gly Asn Tyr
            210                 215                 220

Gly Lys Arg Asp Arg Lys Arg Lys
225                 230

<210> SEQ ID NO 16
<211> LENGTH: 663
<212> TYPE: DNA
<213> ORGANISM: Streptococcus agalactiae

<400> SEQUENCE: 16
atgactcgtt tagaaatagt tgatagcaag ttaagacaag caaaaaaaac agaagaatac      60
ttcaatgcga tccgtacaaa catacagttt agtggaaagg aaaataaaat tcttgcaatt     120
acctctgtta gggaagggga aggaaaatcc actacttcaa caagtttagc tttatcttta     180
gctcaagcag gatttaaaac attattaatt gatgcggata ctaggaactc tgttatgtct     240 ggaacctta aagcaactgg aactattaaa ggcttgacga attatttatc aggtaatgca     300
gatcttggag atattatctg tgaaaccaat gttcctagac tgatggtcgt tccttcaggg     360
aaagtaccac caaatccaac agcattactt cagaacgctt attttaataa gatgattgaa     420
gctattaaaa atatatttga ttatattatc atcgatactc cacctattgg tttagttgtt     480
gatgccgcaa taatctctaa tgcttgcgat ggttttattt tagtaaccca agcaggtaga     540
ataaaacgta attatgttga aaagcaaaa gaacagatgg aacaaagtgg ttcaaagttc     600
ttaggtatta ttcttaataa agttagtgaa tctgttggaa aagggatag aaaaaggaag     660 taa                                                                   663

<210> SEQ ID NO 17
<211> LENGTH: 220
<212> TYPE: PRT
<213> ORGANISM: Streptococcus agalactiae

<400> SEQUENCE: 17

Met Thr Arg Leu Glu Ile Val Asp Ser Lys Leu Arg Gln Ala Lys Lys
1               5                   10                  15

Thr Glu Glu Tyr Phe Asn Ala Ile Arg Thr Asn Ile Gln Phe Ser Gly
            20                  25                  30

Lys Glu Asn Lys Ile Leu Ala Ile Thr Ser Val Arg Glu Gly Glu Gly
        35                  40                  45

Lys Ser Thr Thr Ser Thr Ser Leu Ala Leu Ser Leu Ala Gln Ala Gly
    50                  55                  60

Phe Lys Thr Leu Leu Ile Asp Ala Asp Thr Arg Asn Ser Val Met Ser
65                  70                  75                  80

Gly Thr Phe Lys Ala Thr Gly Thr Ile Lys Gly Leu Thr Asn Tyr Leu
                85                  90                  95

Ser Gly Asn Ala Asp Leu Gly Asp Ile Ile Cys Glu Thr Asn Val Pro
            100                 105                 110

Arg Leu Met Val Val Pro Ser Gly Lys Val Pro Pro Asn Pro Thr Ala
        115                 120                 125

Leu Leu Gln Asn Ala Tyr Phe Asn Lys Met Ile Glu Ala Ile Lys Asn
    130                 135                 140

Ile Phe Asp Tyr Ile Ile Ile Asp Thr Pro Pro Ile Gly Leu Val Val
145                 150                 155                 160

Asp Ala Ala Ile Ile Ser Asn Ala Cys Asp Gly Phe Ile Leu Val Thr
                165                 170                 175

```
Gln Ala Gly Arg Ile Lys Arg Asn Tyr Val Glu Lys Ala Lys Glu Gln
            180                 185                 190

Met Glu Gln Ser Gly Ser Lys Phe Leu Gly Ile Ile Leu Asn Lys Val
        195                 200                 205

Ser Glu Ser Val Gly Lys Arg Asp Arg Lys Arg Lys
        210                 215                 220

<210> SEQ ID NO 18
<211> LENGTH: 33
<212> TYPE: DNA
<213> ORGANISM: Artificial Sequence
<220> FEATURE:
<223> OTHER INFORMATION: PCR Primer

<400> SEQUENCE: 18
taaagcggcc gcctctatca ctgacaacaa tgg                              33

<210> SEQ ID NO 19
<211> LENGTH: 31
<212> TYPE: DNA
<213> ORGANISM: Artificial Sequence
<220> FEATURE:
<223> OTHER INFORMATION: PCR Primer

<400> SEQUENCE: 19
tatcctcgag gaagaagtat attgtggcgt a                                31

<210> SEQ ID NO 20
<211> LENGTH: 32
<212> TYPE: DNA
<213> ORGANISM: Artificial Sequence
<220> FEATURE:
<223> OTHER INFORMATION: PCR Primer

<400> SEQUENCE: 20
ttgttgacgg cgcgaatgat tagacattgt aa                               32

<210> SEQ ID NO 21
<211> LENGTH: 37
<212> TYPE: DNA
<213> ORGANISM: Artificial Sequence
<220> FEATURE:
<223> OTHER INFORMATION: PCR Primer

<400> SEQUENCE: 21
tcgcgccgtc aacaaagaa cacaatggag gaataac                           37

<210> SEQ ID NO 22
<211> LENGTH: 33
<212> TYPE: DNA
<213> ORGANISM: Artificial Sequence
<220> FEATURE:
<223> OTHER INFORMATION: PCR Primer

<400> SEQUENCE: 22
tccatataaa gtagtagcaa cgaaaataga agc                              33

<210> SEQ ID NO 23
<211> LENGTH: 40
<212> TYPE: DNA
<213> ORGANISM: Artificial Sequence
<220> FEATURE:
<223> OTHER INFORMATION: PCR Primer

<400> SEQUENCE: 23
```
actactttat atggataaca agaatgattg atattcattc                                40

<210> SEQ ID NO 24
<211> LENGTH: 36
<212> TYPE: DNA
<213> ORGANISM: Artificial Sequence
<220> FEATURE:
<223> OTHER INFORMATION: PCR Primer

<400> SEQUENCE: 24
accgctaata tagatattaa atacccttc tttatg                                    36

<210> SEQ ID NO 25
<211> LENGTH: 41
<212> TYPE: DNA
<213> ORGANISM: Artificial Sequence
<220> FEATURE:
<223> OTHER INFORMATION: PCR Primer

<400> SEQUENCE: 25
tctatattag cggttaacaa gaatgattga tattcattct c                             41

<210> SEQ ID NO 26
<211> LENGTH: 31
<212> TYPE: DNA
<213> ORGANISM: Artificial Sequence
<220> FEATURE:
<223> OTHER INFORMATION: PCR Primer

<400> SEQUENCE: 26
tttaggatcc caaaagaac gggtgaagga a                                         31

<210> SEQ ID NO 27
<211> LENGTH: 31
<212> TYPE: DNA
<213> ORGANISM: Artificial Sequence
<220> FEATURE:
<223> OTHER INFORMATION: PCR Primer

<400> SEQUENCE: 27
tctactcgag ctaccattac gacctactct a                                        31

<210> SEQ ID NO 28
<211> LENGTH: 36
<212> TYPE: DNA
<213> ORGANISM: Artificial Sequence
<220> FEATURE:
<223> OTHER INFORMATION: PCR Primer

<400> SEQUENCE: 28
gctatcaact atttctaaac gagtcattat attctc                                   36

<210> SEQ ID NO 29
<211> LENGTH: 39
<212> TYPE: DNA
<213> ORGANISM: Artificial Sequence
<220> FEATURE:
<223> OTHER INFORMATION: PCR Primer

<400> SEQUENCE: 29
gaaatagttg atagcaaaag ggatagaaaa aggaagtaa                                39

<210> SEQ ID NO 30
<211> LENGTH: 28
<212> TYPE: DNA

```
<213> ORGANISM: Artificial Sequence
<220> FEATURE:
<223> OTHER INFORMATION: PCR Primer

<400> SEQUENCE: 30
ggaaggggaa ggagcatcca ctacttca                                              28

<210> SEQ ID NO 31
<211> LENGTH: 28
<212> TYPE: DNA
<213> ORGANISM: Artificial Sequence
<220> FEATURE:
<223> OTHER INFORMATION: PCR Primer

<400> SEQUENCE: 31
tgaagtagtg gatgctcctt cccttcc                                               28

<210> SEQ ID NO 32
<211> LENGTH: 40
<212> TYPE: DNA
<213> ORGANISM: Artificial Sequence
<220> FEATURE:
<223> OTHER INFORMATION: PCR Primer

<400> SEQUENCE: 32
aacagattca ctaactttat taagaataat acctaagaac                                 40

<210> SEQ ID NO 33
<211> LENGTH: 36
<212> TYPE: DNA
<213> ORGANISM: Artificial Sequence
<220> FEATURE:
<223> OTHER INFORMATION: PCR Primer

<400> SEQUENCE: 33
gttagtgaat ctgttggaaa aagggataga aaaagg                                     36

<210> SEQ ID NO 34
<211> LENGTH: 20
<212> TYPE: DNA
<213> ORGANISM: Artificial Sequence
<220> FEATURE:
<223> OTHER INFORMATION: PCR Primer

<400> SEQUENCE: 34
aggtttactt gtggcgcttg                                                       20

<210> SEQ ID NO 35
<211> LENGTH: 20
<212> TYPE: DNA
<213> ORGANISM: Artificial Sequence
<220> FEATURE:
<223> OTHER INFORMATION: PCR Primer

<400> SEQUENCE: 35
tctgcttgag caatggtgtc                                                       20

<210> SEQ ID NO 36
<211> LENGTH: 20
<212> TYPE: DNA
<213> ORGANISM: Artificial Sequence
<220> FEATURE:
<223> OTHER INFORMATION: PCR Primer

<400> SEQUENCE: 36
tcaactggac aacgcttcac                                                       20
```

<210> SEQ ID NO 37
<211> LENGTH: 20
<212> TYPE: DNA
<213> ORGANISM: Artificial Sequence
<220> FEATURE:
<223> OTHER INFORMATION: PCR Primer

<400> SEQUENCE: 37
aagttgagct cctggcattg                                              20

<210> SEQ ID NO 38
<211> LENGTH: 20
<212> TYPE: DNA
<213> ORGANISM: Artificial Sequence
<220> FEATURE:
<223> OTHER INFORMATION: PCR Primer

<400> SEQUENCE: 38
tgctcatatg tggcattgtg                                              20

<210> SEQ ID NO 39
<211> LENGTH: 20
<212> TYPE: DNA
<213> ORGANISM: Artificial Sequence
<220> FEATURE:
<223> OTHER INFORMATION: PCR Primer

<400> SEQUENCE: 39
agaaaagata gccggtccac                                              20

<210> SEQ ID NO 40
<211> LENGTH: 148
<212> TYPE: PRT
<213> ORGANISM: Artificial Sequence
<220> FEATURE:
<223> OTHER INFORMATION: CpsA LytR domain aa248-395

<400> SEQUENCE: 40

Arg Ser Asp Val Asn Ile Ile Met Thr Val Asn Thr Asn Thr His Lys
1               5                   10                  15

Val Leu Leu Thr Thr Thr Pro Arg Asp Ala Tyr Val Lys Ile Pro Asp
            20                  25                  30

Gly Gly Gly Asn Gln Tyr Asp Lys Leu Thr His Ala Gly Leu Tyr Gly
        35                  40                  45

Val Glu Thr Ser Met Lys Thr Leu Glu Asn Leu Tyr Asp Ile Asn Leu
    50                  55                  60

Asp Tyr Tyr Ala Arg Ile Asn Phe Ser Ser Phe Leu Lys Leu Ile Asp
65                  70                  75                  80

Leu Leu Gly Gly Val Thr Val Tyr Asn Asp Gln Ala Phe Thr Ser Lys
                85                  90                  95

His Gly Asn Phe Asp Phe Pro Val Gly Gln Val Thr Leu Asn Ser Glu
            100                 105                 110

Gln Ala Leu Gly Phe Val Arg Glu Arg Tyr Ser Leu Gln Gly Gly Asp
        115                 120                 125

Asn Asp Arg Gly Arg Asn Gln Glu Lys Val Ile Ala Ala Ile Ile Asn
    130                 135                 140

Lys Leu Ala Ser
145

<210> SEQ ID NO 41

```
<211> LENGTH: 116
<212> TYPE: PRT
<213> ORGANISM: Artificial Sequence
<220> FEATURE:
<223> OTHER INFORMATION: CpsA PFAM/PPF Domain aa72-187

<400> SEQUENCE: 41

Asn Lys Ala Arg Ile Phe Thr Thr Ile Ile Leu Val Leu Ala Ser Ile
1               5                   10                  15

Phe Val Ala Thr Thr Leu Tyr Gly Phe Lys Ser Thr Ile Asp Leu Thr
            20                  25                  30

Asn Asn Leu Asn Lys Thr Ala Ser Tyr Ser Glu Ile Glu Met Ser Val
            35                  40                  45

Ile Val Pro Lys Asp Ser Lys Ile Thr Asn Ile Glu Ala Val Ser Lys
    50                  55                  60

Leu Ala Ala Pro Val Lys Asn Asp Thr Ser Asn Ile Thr Asp Leu Ile
65                  70                  75                  80

Glu His Ile Lys Ser Glu Lys Gly Ile Ser Ile Thr Pro Gln Lys Thr
                85                  90                  95

Asp Ser Tyr Gln Asp Ala Tyr Asn Arg Ile Lys Asn Gly Asp Ser Gln
            100                 105                 110

Ala Met Val Leu
            115
```